(12) United States Patent
Longo et al.

(10) Patent No.: US 11,364,134 B2
(45) Date of Patent: Jun. 21, 2022

(54) TAPERING STENT

(71) Applicant: Vesper Medical, Inc., Wayne, PA (US)

(72) Inventors: Michael A. Longo, Glenmoore, PA (US); Bruce J. Shook, Devon, PA (US); William James Harrison, Signal Mtn, TN (US)

(73) Assignee: Vesper Medical, Inc., Wayne, PA (US)

(*) Notice: Subject to any disclaimer, the term of this patent is extended or adjusted under 35 U.S.C. 154(b) by 140 days.

(21) Appl. No.: 15/897,673

(22) Filed: Feb. 15, 2018

(65) Prior Publication Data
US 2019/0247209 A1 Aug. 15, 2019

(51) Int. Cl.
*A61F 2/915* (2013.01)
*B24B 5/22* (2006.01)
*A61F 2/958* (2013.01)

(52) U.S. Cl.
CPC ............. *A61F 2/915* (2013.01); *B24B 5/22* (2013.01); *A61F 2/958* (2013.01); *A61F 2002/91516* (2013.01); *A61F 2002/91558* (2013.01); *A61F 2210/0014* (2013.01); *A61F 2240/001* (2013.01); *A61F 2250/0014* (2013.01); *A61F 2250/0018* (2013.01); *A61F 2250/0036* (2013.01); *A61F 2250/0039* (2013.01); *A61F 2250/0098* (2013.01)

(58) Field of Classification Search
CPC ...... A61F 2250/0036; A61F 2250/0029; A61F 2250/0018
See application file for complete search history.

(56) References Cited

U.S. PATENT DOCUMENTS

| | | |
|---|---|---|
| 5,449,373 A | 9/1995 | Pinchasik et al. |
| 5,827,321 A | 10/1998 | Roubin et al. |
| 5,836,966 A | 11/1998 | St. Germain |
| 5,843,120 A | 12/1998 | Israel et al. |
| 5,843,175 A | 12/1998 | Frantzen |
| 5,868,780 A | 2/1999 | Lashinski et al. |
| 5,868,782 A | 2/1999 | Frantzen |
| 5,911,754 A | 6/1999 | Kanesaka et al. |
| 5,922,005 A | 7/1999 | Richter et al. |
| 5,938,697 A | 8/1999 | Killion et al. |

(Continued)

FOREIGN PATENT DOCUMENTS

| | | |
|---|---|---|
| EP | 1579824 A2 | 9/2005 |
| EP | 2174623 A1 | 4/2010 |
| EP | 3043754 A1 | 7/2016 |

OTHER PUBLICATIONS

International Search Report issued in PCT Application No. PCT/US2019/017218; dated May 3, 2019; 13 Pages.

*Primary Examiner* — Jacqueline Woznicki
(74) *Attorney, Agent, or Firm* — Meunier Carlin & Curfman LLC

(57) ABSTRACT

A stent includes a high radial force segment and a highly flexible segment, where the diameters of the high radial force segment and the highly flexible segment are different. For example, the stent may be formed from a tube having varying diameters as it extends distally combined with increased strut density to achieve increased flexibility distally while reducing loss of radial stiffness. The stent may further be placed with an additional stent segment, where the additional stent segment has a radial force similar to the radial force of the highly flexible force segment.

19 Claims, 13 Drawing Sheets

(56) References Cited

U.S. PATENT DOCUMENTS

| | | | |
|---|---|---|---|
| 5,964,798 | A | 10/1999 | Imran |
| 5,972,018 | A | 10/1999 | Israel et al. |
| 6,027,526 | A * | 2/2000 | Limon .............. A61F 2/885 606/194 |
| 6,033,433 | A | 3/2000 | Her et al. |
| 6,042,606 | A | 3/2000 | Frantzen |
| 6,059,811 | A | 5/2000 | Pinchasik et al. |
| 6,068,656 | A | 5/2000 | Von Oepen |
| 6,083,259 | A | 7/2000 | Frantzen |
| 6,106,548 | A | 8/2000 | Roubin et al. |
| 6,113,627 | A | 9/2000 | Jang |
| 6,123,721 | A | 9/2000 | Jang |
| 6,146,403 | A | 11/2000 | St. Germain |
| 6,156,052 | A | 12/2000 | Richter |
| 6,179,868 | B1 | 1/2001 | Burpee et al. |
| 6,183,507 | B1 | 2/2001 | Lashinski et al. |
| 6,190,403 | B1 | 2/2001 | Fischell et al. |
| 6,200,334 | B1 | 3/2001 | Jang |
| 6,203,569 | B1 | 3/2001 | Wijay |
| 6,235,053 | B1 | 5/2001 | Jang |
| 6,241,762 | B1 | 6/2001 | Shanley |
| 6,261,319 | B1 | 7/2001 | Kveen et al. |
| 6,287,336 | B1 | 9/2001 | Globerman et al. |
| 6,299,635 | B1 | 10/2001 | Frantzen |
| 6,309,414 | B1 | 10/2001 | Rolando et al. |
| 6,325,821 | B1 | 12/2001 | Gaschino et al. |
| 6,325,825 | B1 * | 12/2001 | Kula .............. A61F 2/91 623/1.15 |
| 6,402,777 | B1 | 6/2002 | Globerman et al. |
| 6,428,570 | B1 | 8/2002 | Globerman |
| 6,443,982 | B1 | 9/2002 | Israel et al. |
| 6,451,049 | B2 | 9/2002 | Vallana et al. |
| 6,461,380 | B1 | 10/2002 | Cox |
| 6,461,381 | B2 | 10/2002 | Israel et al. |
| 6,464,722 | B2 | 10/2002 | Israel et al. |
| 6,475,236 | B1 | 11/2002 | Roubin |
| 6,478,816 | B1 | 11/2002 | Kveen et al. |
| 6,485,508 | B1 | 11/2002 | McGuinness |
| 6,485,509 | B2 | 12/2002 | Killion et al. |
| 6,497,723 | B1 | 12/2002 | Starck et al. |
| 6,540,775 | B1 | 4/2003 | Fischell et al. |
| 6,635,084 | B2 | 10/2003 | Israel et al. |
| 6,638,300 | B1 | 10/2003 | Frantzen |
| 6,641,609 | B2 | 11/2003 | Globerman |
| 6,660,019 | B1 | 12/2003 | Richter et al. |
| 6,679,911 | B2 | 1/2004 | Burgermeister |
| 6,682,554 | B2 | 1/2004 | Von Oepen et al. |
| 6,692,522 | B1 | 2/2004 | Richter |
| 6,699,281 | B2 | 3/2004 | Vallana et al. |
| 6,706,061 | B1 | 3/2004 | Fischell et al. |
| 6,709,453 | B2 | 3/2004 | Pinchasik et al. |
| 6,730,116 | B1 | 5/2004 | Wolinsky et al. |
| 6,746,479 | B2 | 6/2004 | Her et al. |
| 6,761,731 | B2 | 7/2004 | Majercak |
| 6,764,506 | B2 | 7/2004 | Roubin et al. |
| 6,786,922 | B2 | 9/2004 | Schaeffer |
| 6,790,227 | B2 | 9/2004 | Burgermeister |
| 6,818,015 | B2 | 11/2004 | Hankh et al. |
| 6,923,829 | B2 | 8/2005 | Boyle et al. |
| 6,939,373 | B2 | 9/2005 | Gomez et al. |
| 6,945,993 | B2 | 9/2005 | Kveen et al. |
| 7,004,968 | B2 | 2/2006 | Lootz et al. |
| 7,029,493 | B2 | 4/2006 | Majercak et al. |
| 7,037,330 | B1 | 5/2006 | Rivelli, Jr. et al. |
| 7,060,088 | B1 | 6/2006 | Fischell et al. |
| 7,060,090 | B2 | 6/2006 | Thornton |
| 7,070,614 | B1 | 7/2006 | Neuss et al. |
| 7,131,993 | B2 | 11/2006 | Gregorich |
| 7,141,062 | B1 | 11/2006 | Pinchasik et al. |
| 7,273,494 | B2 | 9/2007 | Rolando et al. |
| 7,316,710 | B1 | 1/2008 | Cheng et al. |
| 7,326,243 | B2 | 2/2008 | Kveen et al. |
| 7,344,563 | B2 | 3/2008 | Vallana et al. |
| 7,357,813 | B2 | 4/2008 | Burgermeister |
| 7,402,169 | B2 | 7/2008 | Killion |
| 7,485,130 | B2 | 2/2009 | St. Germain |
| 7,527,644 | B2 | 5/2009 | Mangiardi et al. |
| 7,621,947 | B2 | 11/2009 | Richter et al. |
| 7,648,526 | B2 | 1/2010 | Sano et al. |
| 7,686,843 | B2 | 3/2010 | Moore |
| 7,731,746 | B2 | 6/2010 | Kveen et al. |
| 7,806,918 | B2 | 10/2010 | Nissl et al. |
| 7,862,607 | B2 | 1/2011 | McDermott et al. |
| 7,896,912 | B2 | 3/2011 | Shanley |
| 8,012,196 | B2 | 9/2011 | Smith et al. |
| 8,016,874 | B2 | 9/2011 | Casey |
| 8,128,679 | B2 | 3/2012 | Casey |
| 8,206,427 | B1 | 6/2012 | Ryan et al. |
| 8,211,163 | B2 | 7/2012 | Dakin et al. |
| 8,221,489 | B2 | 7/2012 | Issenmann et al. |
| 8,257,424 | B2 | 9/2012 | Orlowski |
| 8,267,991 | B2 | 9/2012 | De Scheerder et al. |
| 8,317,854 | B1 | 11/2012 | Ryan et al. |
| 8,317,859 | B2 | 11/2012 | Snow et al. |
| 8,337,544 | B2 | 12/2012 | Osman et al. |
| 8,348,990 | B2 | 1/2013 | Boyle et al. |
| 8,470,021 | B2 | 6/2013 | Magnuson et al. |
| 8,524,132 | B2 | 9/2013 | Von Oepen et al. |
| 8,562,665 | B2 | 10/2013 | Jang |
| 8,647,379 | B2 | 2/2014 | McDermott et al. |
| 8,652,196 | B2 | 2/2014 | Nissl |
| 8,668,731 | B2 | 3/2014 | Kveen et al. |
| 8,888,837 | B2 | 11/2014 | Obradović et al. |
| 8,974,514 | B2 | 3/2015 | Anukhin et al. |
| 9,066,825 | B2 | 6/2015 | Chanduszko |
| 9,320,627 | B2 | 4/2016 | Casey |
| 9,375,810 | B2 | 6/2016 | Mangiardi |
| 9,408,727 | B2 | 8/2016 | Ainsworth et al. |
| 9,498,360 | B2 | 11/2016 | Layman et al. |
| 9,554,927 | B2 | 1/2017 | Bales, Jr. et al. |
| 9,561,123 | B2 | 2/2017 | Bales, Jr. et al. |
| 9,622,850 | B2 | 4/2017 | Bebb |
| 9,649,211 | B2 | 5/2017 | Bonsignore et al. |
| 9,655,998 | B2 | 5/2017 | Gemborys |
| 9,668,895 | B2 | 6/2017 | Dreher |
| 9,668,898 | B2 | 6/2017 | Wong |
| 9,693,860 | B2 | 7/2017 | Sandstrom et al. |
| 9,700,448 | B2 | 7/2017 | Snow et al. |
| 9,707,110 | B2 | 7/2017 | McDermott et al. |
| 9,724,220 | B2 | 8/2017 | Rasmussen |
| 9,770,348 | B2 | 9/2017 | Wack |
| 9,795,496 | B2 | 10/2017 | Armstrong et al. |
| 9,839,538 | B2 | 12/2017 | Grewe et al. |
| 9,839,540 | B2 | 12/2017 | Armstrong et al. |
| 2001/0014822 | A1 | 8/2001 | Milo |
| 2001/0047200 | A1 | 11/2001 | White et al. |
| 2002/0013616 | A1 | 1/2002 | Carter et al. |
| 2002/0042648 | A1 | 4/2002 | Schaldach et al. |
| 2002/0058990 | A1 | 5/2002 | Jang |
| 2003/0009214 | A1 | 1/2003 | Shanley |
| 2003/0014102 | A1 | 1/2003 | Hong et al. |
| 2003/0100941 | A1 | 5/2003 | Fischell et al. |
| 2003/0105513 | A1 | 6/2003 | Moriuchi et al. |
| 2003/0105517 | A1 | 6/2003 | White et al. |
| 2004/0054398 | A1 | 3/2004 | Cully et al. |
| 2004/0054400 | A1 | 3/2004 | Granada |
| 2004/0102835 | A1 | 5/2004 | Israel et al. |
| 2004/0133265 | A1 | 7/2004 | Duffy |
| 2004/0254627 | A1 | 12/2004 | Thompson et al. |
| 2004/0267350 | A1 | 12/2004 | Roubin et al. |
| 2005/0004657 | A1 | 1/2005 | Burgermeister |
| 2005/0021130 | A1 | 1/2005 | Kveen et al. |
| 2005/0060024 | A1 | 3/2005 | Lee et al. |
| 2005/0080479 | A1 | 4/2005 | Feng et al. |
| 2006/0025852 | A1 | 2/2006 | Armstrong et al. |
| 2006/0129227 | A1 | 6/2006 | Hengelmolen |
| 2006/0173531 | A1 | 6/2006 | Richter |
| 2007/0010869 | A1 | 1/2007 | Sano |
| 2007/0185563 | A1 | 8/2007 | Zarbatany et al. |
| 2007/0213806 | A1 | 9/2007 | Roubin et al. |
| 2007/0213807 | A1 | 9/2007 | Roubin et al. |
| 2007/0219613 | A1 | 9/2007 | Kao et al. |
| 2008/0009938 | A1 | 1/2008 | Huang et al. |
| 2008/0051878 | A1 | 2/2008 | Cheng et al. |

(56) References Cited

U.S. PATENT DOCUMENTS

| | | |
|---|---|---|
| 2008/0140181 A1 | 6/2008 | Reynolds et al. |
| 2008/0288048 A1 | 11/2008 | Rolando et al. |
| 2009/0018641 A1 | 1/2009 | Binkert |
| 2009/0062899 A1 | 3/2009 | Dang et al. |
| 2010/0004736 A1 | 1/2010 | Rolando et al. |
| 2010/0222864 A1 | 9/2010 | Rivelli, Jr. et al. |
| 2010/0241216 A1 | 9/2010 | Rolando et al. |
| 2011/0125251 A1 | 2/2011 | Cottone et al. |
| 2011/0106237 A1 | 5/2011 | Bonsignore et al. |
| 2011/0152994 A1* | 6/2011 | Hendriksen ............... A61F 2/91 623/1.11 |
| 2011/0230957 A1 | 9/2011 | Bonsignore et al. |
| 2012/0043703 A1 | 2/2012 | Von Oepen et al. |
| 2012/0046729 A1 | 2/2012 | Von Oepen et al. |
| 2012/0046730 A1 | 2/2012 | Von Oepen et al. |
| 2012/0046731 A1 | 2/2012 | Von Oepen et al. |
| 2012/0046733 A1 | 2/2012 | Von Oepen et al. |
| 2012/0046739 A1 | 2/2012 | Von Oepen et al. |
| 2012/0143312 A1 | 6/2012 | Brown |
| 2012/0277844 A1 | 11/2012 | Wu |
| 2012/0310327 A1 | 12/2012 | McHugo |
| 2013/0178928 A1 | 7/2013 | Vyas et al. |
| 2013/0304192 A1 | 11/2013 | Chanduszko |
| 2013/0325141 A1 | 12/2013 | Gill et al. |
| 2014/0277365 A1 | 9/2014 | Gillespie |
| 2014/0277378 A1 | 9/2014 | Lane et al. |
| 2015/0105852 A1 | 4/2015 | Noffke et al. |
| 2015/0209167 A1 | 7/2015 | Mangiardi |
| 2015/0250580 A1 | 9/2015 | Besselink |
| 2015/0265438 A1* | 9/2015 | Hossainy ............... A61F 2/89 623/1.11 |
| 2015/0305943 A1 | 10/2015 | Hossainy et al. |
| 2016/0235562 A1 | 8/2016 | Casey |
| 2016/0250052 A1 | 9/2016 | Kaspar |
| 2016/0287418 A1 | 10/2016 | Cheng et al. |
| 2017/0035548 A1 | 2/2017 | Bebb et al. |
| 2017/0071768 A1 | 3/2017 | Krieger et al. |
| 2017/0086994 A1 | 3/2017 | Bales et al. |
| 2017/0100267 A1 | 4/2017 | Bales et al. |
| 2017/0224878 A1 | 8/2017 | Gemborys |
| 2017/0265998 A1 | 9/2017 | Sandstrom et al. |
| 2017/0312104 A1 | 11/2017 | McDermott et al. |
| 2017/0312105 A1 | 11/2017 | McDermott et al. |
| 2017/0340464 A1 | 11/2017 | Kovach et al. |

\* cited by examiner

TAPERING STENT

BACKGROUND

Field of the Invention

Disclosed herein are stents for implantation within the body and methods for delivery and/or deployment. Certain embodiments disclosed herein may be used in procedures to treat May-Thurner syndrome and/or deep venous thrombosis and the resulting post-thrombotic syndrome.

Description of the Related Art

May-Thurner syndrome, also known as iliac vein compression syndrome, is a condition in which compression of the common venous outflow tract of the left lower extremity may cause various adverse effects, including, but not limited to, discomfort, swelling, pain, and/or deep venous thrombosis (DVT) (commonly known as blood clots). May-Thurner syndrome occurs when the left common iliac vein is compressed by the overlying right common iliac artery, leading to stasis of blood, which may cause the formation of blood clots in some individuals. Other, less common, variations of May-Thurner syndrome have been described, such as compression of the right common iliac vein by the right common iliac artery.

While May-Thurner syndrome is thought to represent between two to five percent of lower-extremity venous disorders, it frequently goes unrecognized. Nevertheless, it is generally accepted that May-Thurner syndrome is about three times more common in women than it is in men and typically manifests itself between the age of twenty and forty. Patients exhibiting both hypercoagulability and left lower extremity thrombosis may be suffering from May-Thurner syndrome. To confirm that diagnosis, it may be necessary to rule out other causes for hypercoagulable state, for example by evaluating levels of antithrombin, protein C, protein S, factor V Leiden, and prothrombin G20210A.

By contrast to the right common iliac vein, which ascends almost vertically parallel to the inferior vena cava, the left common iliac vein takes a more transverse course. Along this course, it lies under the right common iliac artery, which may compress it against the lumbar spine. Iliac vein compression is a frequent anatomic variant—it is thought that as much as 50% luminal compression of the left iliac vein occurs in a quarter of healthy individuals. However, compression of the left common iliac vein becomes clinically significant only if such compression causes appreciable hemodynamic changes in venous flow or venous pressure, or if it leads to acute or chronic deep venous thrombosis, which will be discussed in more detail below. In addition to the other problems associated with compression, the vein may also develop intraluminal fibrous spurs from the effects of the chronic pulsatile compressive force from the overlying artery.

The narrowed, turbulent channel associated with May-Thurner syndrome may predispose the afflicted patient to thrombosis. And, the compromised blood flow often causes collateral blood vessels to form—most often horizontal transpelvis collaterals, connecting both internal iliac veins to create additional outflow possibilities through the right common iliac vein. Sometimes vertical collaterals are formed, most often paralumbar, which can cause neurological symptoms, like tingling and numbness.

Current best practices for the treatment and/or management of May-Thurner syndrome is proportional to the severity of the clinical presentation. Leg swelling and pain is best evaluated by vascular specialists, such as vascular surgeons, interventional cardiologists, and interventional radiologists, who both diagnose and treat arterial and venous diseases to ensure that the cause of the extremity pain is evaluated. Diagnosis of May-Thurner syndrome is generally confirmed one or more imaging modalities that may include magnetic resonance venography, and venogram, which, because the collapsed/flattened left common iliac may not be visible or noticed using conventional venography, are usually confirmed with intravascular ultrasound. To prevent prolonged swelling or pain as downstream consequences of the left common iliac hemostasis, blood flow out of the leg should be improved/increased. Early-stage or uncomplicated cases may be managed simply with compression stockings. Late-stage or severe May-Thurner syndrome may require thrombolysis if there is a recent onset of thrombosis, followed by angioplasty and stenting of the iliac vein after confirming the diagnosis with a venogram or an intravascular ultrasound. A stent may be used to support the area from further compression following angioplasty. However, currently available stenting options suffer from several complications—including severe foreshortening, lack of flexibility (which can force the vessel to straighten excessively), vessel wear and eventual perforation, increased load on and deformation of the stent causing early fatigue failure, and/or impedence of flow in the overlying left iliac artery potentially causing peripheral arterial disease. The compressed, narrowed outflow channel present in May-Thurner syndrome may cause stasis of the blood, which an important contributing factor to deep vein thrombosis.

Some patients suffering from May-Thurner syndrome may exhibit thrombosis while others may not. Nevertheless, those patients that do not experience thrombotic symptoms may still experience thrombosis at any time. If a patient has extensive thrombosis, pharmacologic and/or mechanical (i.e., pharmacomechanical) thrombectomy may be necessary. The hemostasis caused by May-Thurner syndrome has been positively linked to an increased incidence of deep vein thrombosis ("DVT").

Deep vein thrombosis, or deep venous thrombosis, is the formation of a blood clot (thrombus) within a deep vein, predominantly in the legs. The right and left common iliac are common locations for deep vein thrombosis, but other locations of occurrence are common. Non-specific symptoms associated with the condition may include pain, swelling, redness, warmness, and engorged superficial veins. Pulmonary embolism, a potentially life-threatening complication of deep vein thrombosis, is caused by the detachment of a partial or complete thrombus that travels to the lungs. Post-thrombotic syndrome, another long-term complication associated with deep venous thrombosis, is a medical condition caused by a reduction in the return of venous blood to the heart and can include the symptoms of chronic leg pain, swelling, redness, and ulcers or sores.

Deep vein thrombosis formation typically begins inside the valves of the calf veins, where the blood is relatively oxygen deprived, which activates certain biochemical pathways. Several medical conditions increase the risk for deep vein thrombosis, including cancer, trauma, and antiphospholipid syndrome. Other risk factors include older age, surgery, immobilization (e.g., as experienced with bed rest, orthopedic casts, and sitting on long flights), combined oral contraceptives, pregnancy, the postnatal period, and genetic factors. Those genetic factors include deficiencies with antithrombin, protein C, and protein S, the mutation of Factor V Leiden, and the property of having a non-O blood type. The rate of new cases of deep vein thrombosis increases dramatically from childhood to old age; in adulthood, about 1 in 1000 adults develops the condition annually.

Common symptoms of deep vein thrombosis include pain or tenderness, swelling, warmth, redness or discoloration, and distention of surface veins, although about half of those with the condition have no symptoms. Signs and symptoms alone are not sufficiently sensitive or specific to make a diagnosis, but when considered in conjunction with known risk factors can help determine the likelihood of deep vein thrombosis. Deep vein thrombosis is frequently ruled out as a diagnosis after patient evaluation: the suspected symptoms are more often due to other, unrelated causes, such as cellulitis, Baker's cyst, musculoskeletal injury, or lymphedema. Other differential diagnoses include hematoma, tumors, venous or arterial aneurysms, and connective tissue disorders.

Anticoagulation, which prevents further coagulation but does not act directly on existing clots, is the standard treatment for deep vein thrombosis. Other, potentially adjunct, therapies/treatments may include compression stockings, selective movement and/or stretching, inferior vena cava filters, thrombolysis, and thrombectomy.

In any case, treatment of various venous maladies, including those described above, can be improved with stents. Improvements in stents for venous use are therefore desired.

BRIEF SUMMARY OF THE INVENTION

Accordingly, the present invention is directed to an intravascular stent that obviates one or more of the problems due to limitations and disadvantages of the related art.

In one embodiment, a stent includes an elongate tubular wall structure including a firm region, a transition region and a flexible region. The firm region has a thicker wall structure than the transition region. The transition region has a thicker wall structure than the flexible region. In this manner, the radial stiffness of the stent in the firm region is greater than the radial stiffness of the flexible region while the flexibility of the flexible region at the other end of the stent is greater than the firm region. In this manner, the stent has increased radial stiffness to mediate venous maladies such as May-Thurner Syndrome on a proximal end while the distal end of the stent is sufficiently flexible to survive high bending loads and tortuous venous passageways. Even further advantageously, the structure of the stent, such as the density and number of interconnections of the struts, can be adapted to reduce the loss of radial strength resulting from the reduction of wall thickness (corresponding to strut thickness) in the distal direction. Thus, the stent can achieve a "goldilocks" state of high flexibility without a concomitant loss of radial stiffness useful for a range of applications.

The elongate tubular wall structure in another embodiment can define a lumen extending therethrough. The elongate tubular wall structure has a firm region, a transition region and a flexible region in that order, extending distally. The firm region has a first thickness, the transition region a second thickness and the flexible region a third thickness. The first thickness is greater than the third thickness. This contributes to a radial stiffness of the firm region being greater than a radial stiffness of the flexible region.

In another aspect, the second thickness is less than the first thickness but greater than the third thickness. This contributes to a radial stiffness of the transition region being less than the firm region but greater than the flexible region.

The elongate tubular wall structure may also include an inside diameter, wherein the first thickness is between a first diameter and the inside diameter, the second thickness is between a second diameter and the inside diameter, and the third thickness is between a third diameter and the inside diameter. In another aspect, the radial stiffness of the firm region is adapted to mediate May-Thurner Syndrome. The inside diameter may be a constant diameter.

In another aspect, the flexible region can have a flexibility that is greater than a flexibility of the firm region. Also, the transition region may have a flexibility that is greater than the flexibility of the firm region and less than the flexibility of the flexible region.

In another embodiment, a difference between the flexibility of the flexible region and the firm region is greater than a difference between the radial stiffness of the firm region and the radial stiffness of the flexible region. The flexibility of the elongate tubular wall structure can increase faster than radial stiffness drops progressing from the firm region toward the flexible region.

The elongate tubular wall structure may be defined by a plurality of interconnected struts. The interconnected struts may have a greater density in the flexible region than the firm region to mediate the loss of radial stiffness resulting from decreased wall thickness. Also, alternatively or in addition, the interconnected struts may have a greater frequency of interconnection in the flexible region than the firm region.

In another embodiment, a method of making a medical device includes selecting an elongate tubular structure defining a lumen therethrough and having a constant inside diameter and outside diameter. Also, the method includes grinding an outside of an elongate tubular structure to create a third diameter of a flexible region that is less than a first diameter of a firm region. Further, cutting a plurality of struts out of the elongate tubular structure. The grinding and cutting contribute to the firm region having a radial stiffness greater than a radial stiffness of the flexible region and a flexibility lesser than a flexibility of the flexible region. Grinding may include centerless grinding, for example.

In another aspect, grinding of the elongate tubular structure includes grinding a second diameter of a transition region to be less than the first diameter of the firm region and greater than the third diameter of the flexible region.

Cutting the plurality of the struts can include cutting struts with more connections in the flexible region than in the firm region. Also, cutting the plurality of struts can include cutting struts with fewer connections in the transition region than the firm region and more connections in the transition region than the flexible region.

Cutting the plurality of struts, for example, can mediate a proportional loss of radial stiffness in a distal direction along the elongate tubular structure to be less than a proportional increase in flexibility in the distal direction.

The method can also include stiffening a first and second free ends of the stent to have a radial stiffness greater than the firm, transition and flexible regions extending therebetween.

The method can further include compression the medical device into a delivery catheter.

Further embodiments, features, and advantages of the intravascular stent, as well as the structure and operation of the various embodiments of the intravascular stent, are described in detail below with reference to the accompanying drawings.

It is to be understood that both the foregoing general description and the following detailed description are exemplary and explanatory only, and are not restrictive of the invention as claimed.

BRIEF DESCRIPTION OF THE DRAWINGS

The accompanying figures, which are incorporated herein and form part of the specification, illustrate an intravascular stent. Together with the description, the figures further serve to explain the principles of the intravascular stent described herein and thereby enable a person skilled in the pertinent art to make and use the intravascular stent.

DETAILED DESCRIPTION

Accurate placement is ideal in all medical interventions, but it is vital in areas where the end that is first deployed is critical. Such areas include at vessel bifurcations and branch vessels, so that the implant does not enter or interfere with the portion of the vessel that does not require treatment. Such a bifurcation is present at the inferior vena cava where it branches into right and left iliac veins, as described in more detail below.

Figure 1:
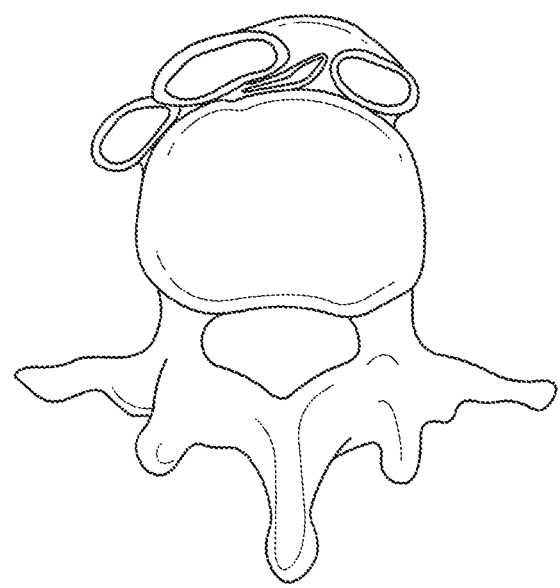
FIG. 1 shows an inferior-posterior view of the L5 lumbar and the bifurcations of the abdominal aorta and inferior vena cava.

May-Thurner syndrome, or iliac vein compression syndrome, occurs in the peripheral venous system when the iliac artery compresses the iliac vein against the spine as shown in FIG. 1. FIG. 1 illustrates a vertebra, the right and left common iliac arteries near the bifurcation of the abdominal aorta, and the right and left common iliac arteries near the bifurcation of the inferior vena cava. The bifurcations generally occur near the L5 lumbar vertebra. Thus, it can be seen that FIG. 1 shows an inferior-posterior view of the L5 lumbar and the bifurcations of the abdominal aorta and inferior vena cava.

As shown, the strong right common iliac artery has compressed the iliac vein causing it to become narrowed. This is one possible, if not a classic, manifestation of May-Thurner syndrome. Over time, such narrowing may cause vascular scarring which can result in intraluminal changes that could precipitate iliofemoral venous outflow obstruction and/or deep vein thrombosis. As discussed above, venous insufficiency (i.e., a condition in which the flow of blood through the veins is impaired) can ultimately lead to various deleterious pathologies including, but not limited to, pain, swelling, edema, skin changes, and ulcerations. Venous insufficiency is typically brought on by venous hypertension that develops as a result of persistent venous obstruction and incompetent (or subcompetent) venous valves. Current treatments for venous outflow obstruction include anticoagulation, thrombolysis, balloon angioplasty and stenting.

Figure 2:
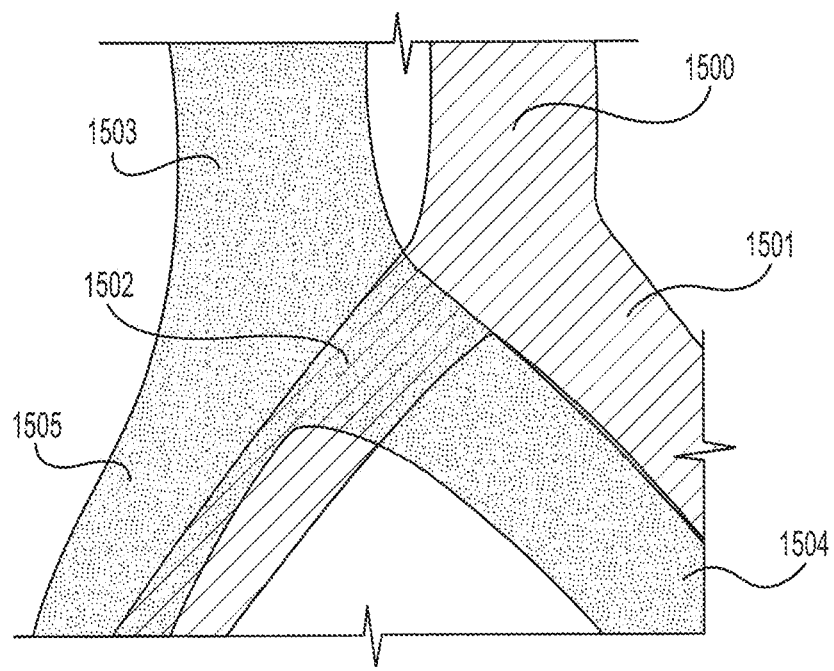
FIG. 2 shows a schematic of the standard overlap of the right common iliac artery over the left common iliac vein.

FIG. 2 illustrates the standard overlap of the right common iliac artery over the left common iliac vein. The arteries shown include the abdominal aorta 1500 branching into the left common iliac artery 1501 and the right common iliac artery 1502. The veins shown include the inferior vena cava 1503 branching into the left common iliac vein 1504 and right common iliac vein 1505. It will be understood that the rough diagram illustrated in FIG. 2 represents the view looking down on a patient laying face-up (i.e., an anterior-poster view of the patient at the location of the bifurcation of the abdominal aorta 1500 and the inferior vena cava 1503). The overlap of the right common iliac artery 1502, which is relatively strong and muscular, over the left common iliac vein 1504 can cause May-Thurner syndrome by pressing down on the vein 1504, crushing it against the spine, restricting flow, and, eventually, causing thrombosis and potentially partially or completely clotting off of the left common iliac vein 1504 and everything upstream of it (i.e., the venous system in the left leg, among others).

Figure 3:
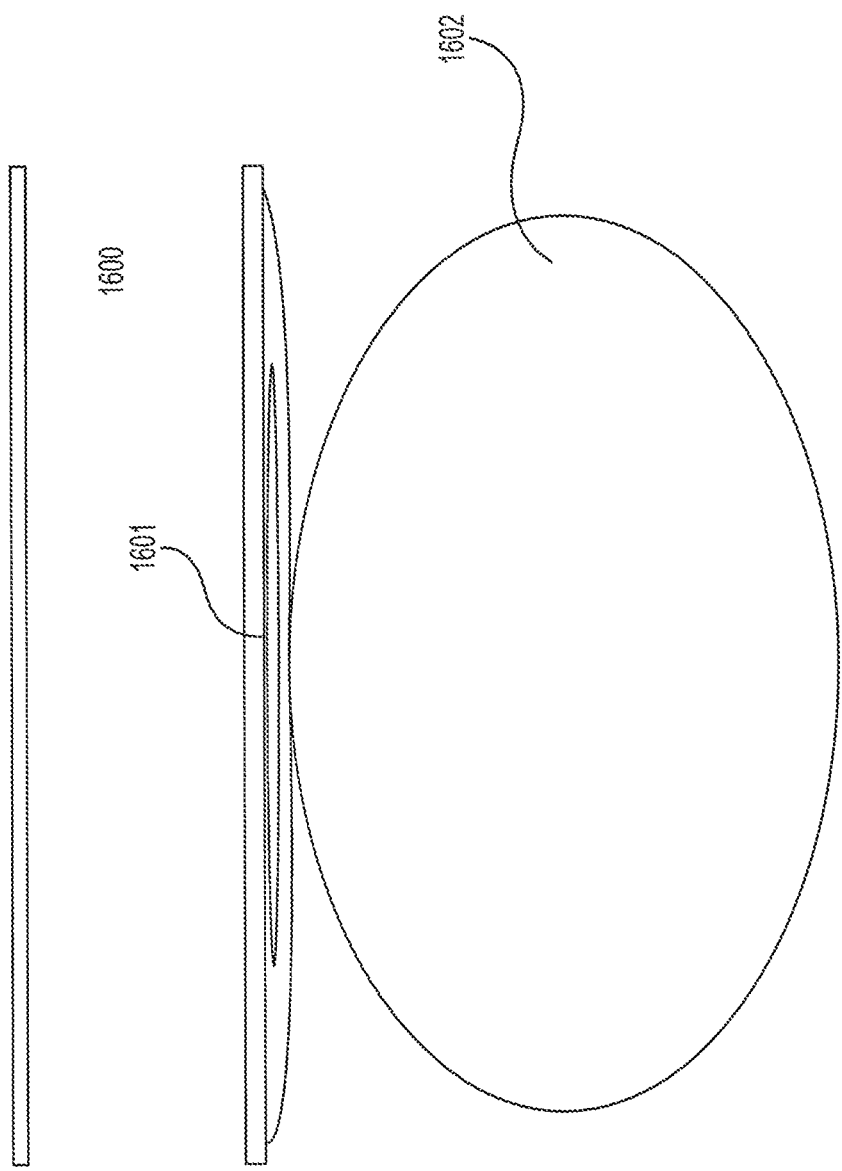
FIG. 3 shows a cross-sectional schematic of the arterio-venous system shown in FIG. 2.

FIG. 3 illustrates a cross-section of the arterio-venous system shown in FIG. 2 taken along the gray dotted line. Shown in schematic are the right common iliac artery 1600, the left common iliac vein 1601, and a vertebra 1602 of the spine (possibly the L5 lumbar vertebra of the lumbar spine). As can be seen, the right common iliac artery 1600 is substantially cylindrical, due to its strong, muscular construction (among other potential factors). That strong, muscular artery has pressed down on the left common iliac vein 1601, until it has almost completely lost patency, i.e., it is nearly completely pinched off. It will be understood that May-Thurner syndrome may indeed involve such severe pinching/crushing of the underlying left common iliac vein 1601 against the vertebra 1602 of the lumbar spine. However, it will also be understood that May-Thurner syndrome may involve much less pinching/crushing of the underlying left common iliac vein 1601 against the vertebra 1602. Indeed, embodiments disclosed herein are appropriate for the treatment of various degrees of May-Thurner syndrome, including full crushing/pinching of the left common iliac vein 1602 by the right common iliac artery 1600. Other embodiments disclosed herein are appropriate for the treatment of various degrees of May-Thurner syndrome, including, but not limited to a crush/pinch of the underlying left common iliac vein 1601 of between about 10-95%, about 15-90%, about 20-85%, about 25-80%, about 30-75%, about 35-70%, about 40-65%, about 45-60%, and about 50-55%, or any other crush/pinch that could merit treatment using one or more of the devices disclosed herein.

Generally, disclosed herein are stents that include circumferential rings of alternating interconnected struts connected by flexible connectors. The stent may have open or closed cells of various configuration formed by an expandable material. The final expanded implanted configuration can be achieved through mechanical expansion/actuation (e.g., balloon-expandable) or self-expansion (e.g., Nitinol). An exemplary embodiment of the stents described herein are self-expanding implants comprising super elastic or shape memory alloy materials, but the stent is not so limited and may be formed of balloon-expandable material. According to an aspect of the present disclosure, an expandable stent has varying magnitudes of radial force, crush resistance and flexibility at different locations along the length of the stent, while at the same time, the different locations have the same or similar diameter in an expanded configuration of the stent.

Figure 6:
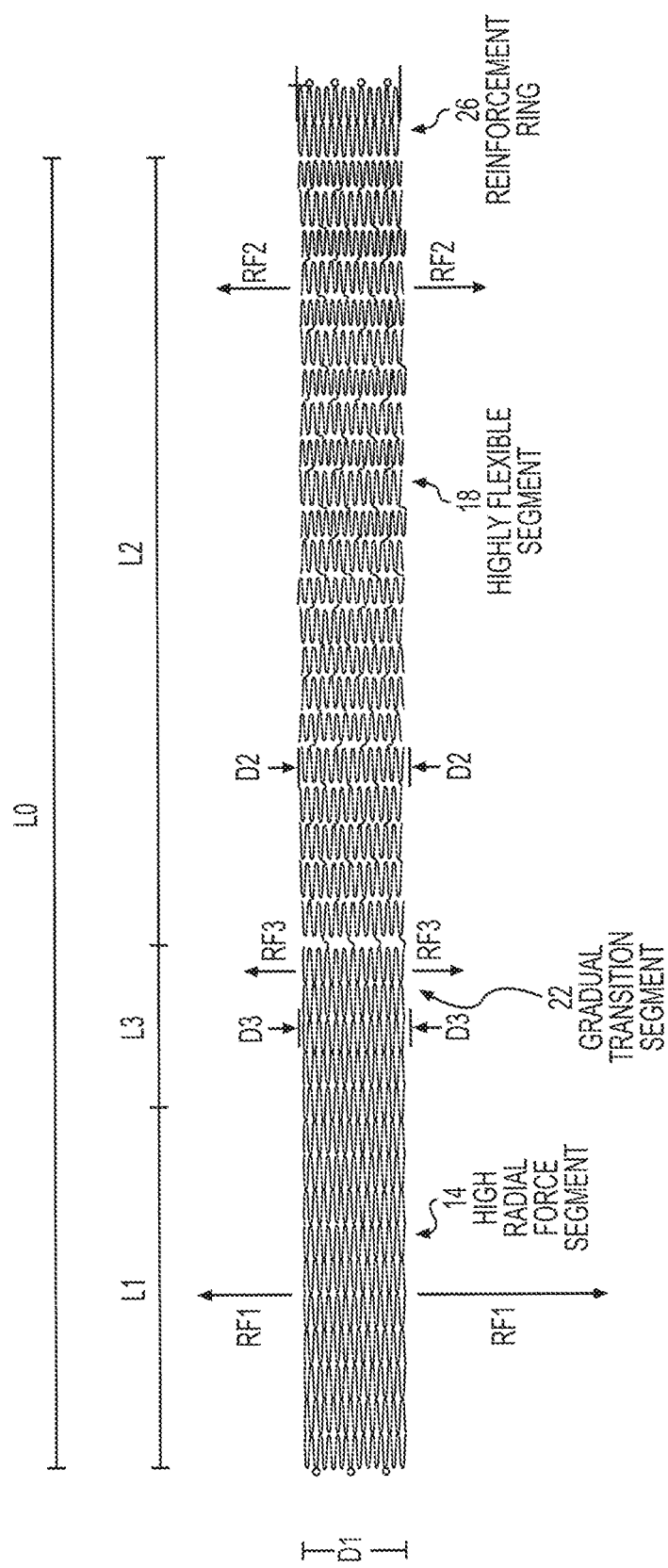
FIG. 6 illustrates an exemplary hybrid stent according to principles of the present disclosure.

As illustrated in FIG. 6, an exemplary stent 10 includes a high radial force segment 14, a highly flexible segment 18 and a transition segment 22 between the high radial force segment 14 and the highly flexible segment 18. The exemplary stent 10, as illustrated in FIG. 6, may include a reinforcement ring 26 at an end of the stent 10, for example, adjacent the highly flexible segment 18 (configuration shown) or adjacent the high radial force segment 14 (configuration not shown). In an embodiment according to principles described herein, the stent 10 having a high radial force segment 14 and a highly flexible segment 18 may be cut from a single tube, such as nitinol, for example, but could also be formed or cut from flat sheets that are welded together at long edges to form a tube-like structure. While a transition segment is illustrated herein, it should be noted that a hybrid stent that does not include a transition segment is considered to be within the scope of this disclosure.

Figure 4:
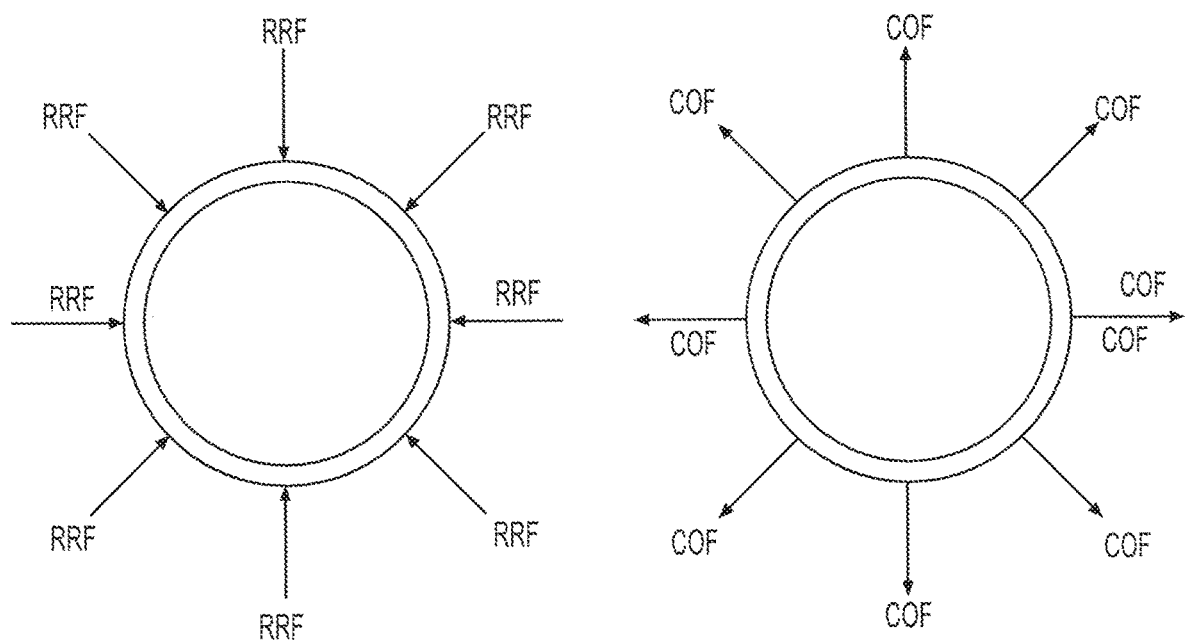
FIG. 4 illustrates radial force as radial resistive force or chronic outward force.
Figure 5:
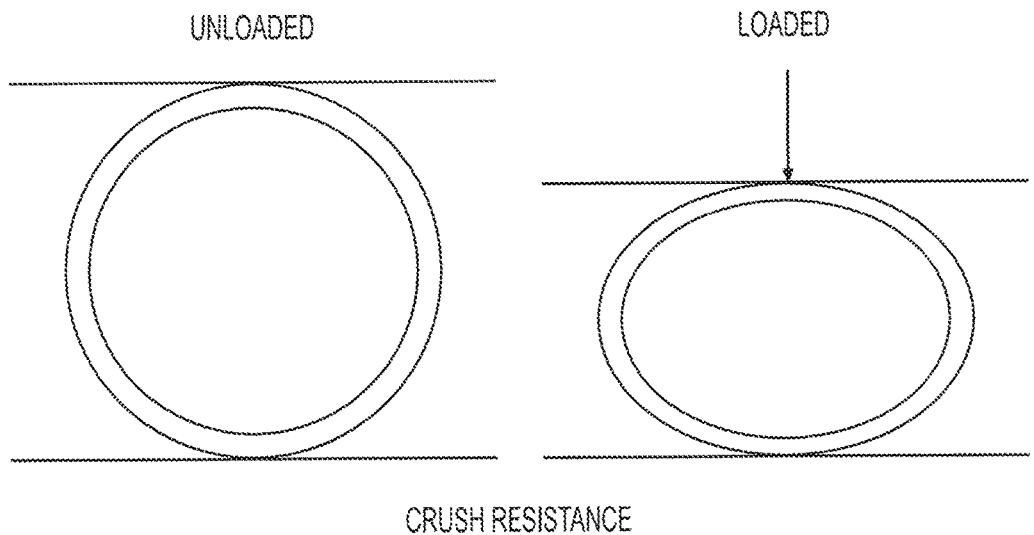
FIG. 5 illustrates crush resistance force and load on an exemplary stent.

Generally radial force refers to both or either Radial Resistive Force (RRF) and Chronic Outward Force (COF). As shown in FIG. 4, radial resistive force is an external force that acts around the circumference of a stent on the stent (toward the center of the stent). Chronic outward force is the force the sent exerts outward from a direction of the center of the stent. Chronic outward force of a stent will cause the stent to exert force on the vessel in which it is inserted to resist collapse and keep the vessel open. FIG. 5 illustrates crush resistance, as used herein. Crush resistance is a force of the stent when subject to a flat plate/focal crush load. While the radial force vector directions in FIG. 6 illustrate chronic outward force, the radial force according to principles of the present disclosure may be radial resistive force, which is more related to crush resistance than a chronic outward force. Vectors illustrated in the figures are meant to indicate direction, not magnitude. Although Radial Force and Crush Resistance can be related they do not necessarily drive each other. So, a stent may be designed to have high crush resistance (flat plate/focal) but not high radial force. Such attributes can be tested independently in different test configurations.

The reinforcement ring may be an area of greater stiffness/crush resistance at an end portion of the stent. "Greater stiffness" here means having a stiffness/crush resistance greater than a portion of the stent adjacent the reinforcement ring. The reinforcement ring having greater stiffness may provide good inflow into the stent and through the vessel having the implant therein. While described herein as a "reinforcement ring," the area of greater stiffness may be provided by an additional structure overlying the stent end (e.g., a "ring") or may instead be an area where the strut structure is actually stronger, e.g., because the material forming the area of greater stiffness is inherently stiffer, a tighter cell structure, thicker struts or the like. For example, the reinforcement ring may have a different stent geometry, e.g., different strut width or is simply a fully-connected ring.

Figure 7:
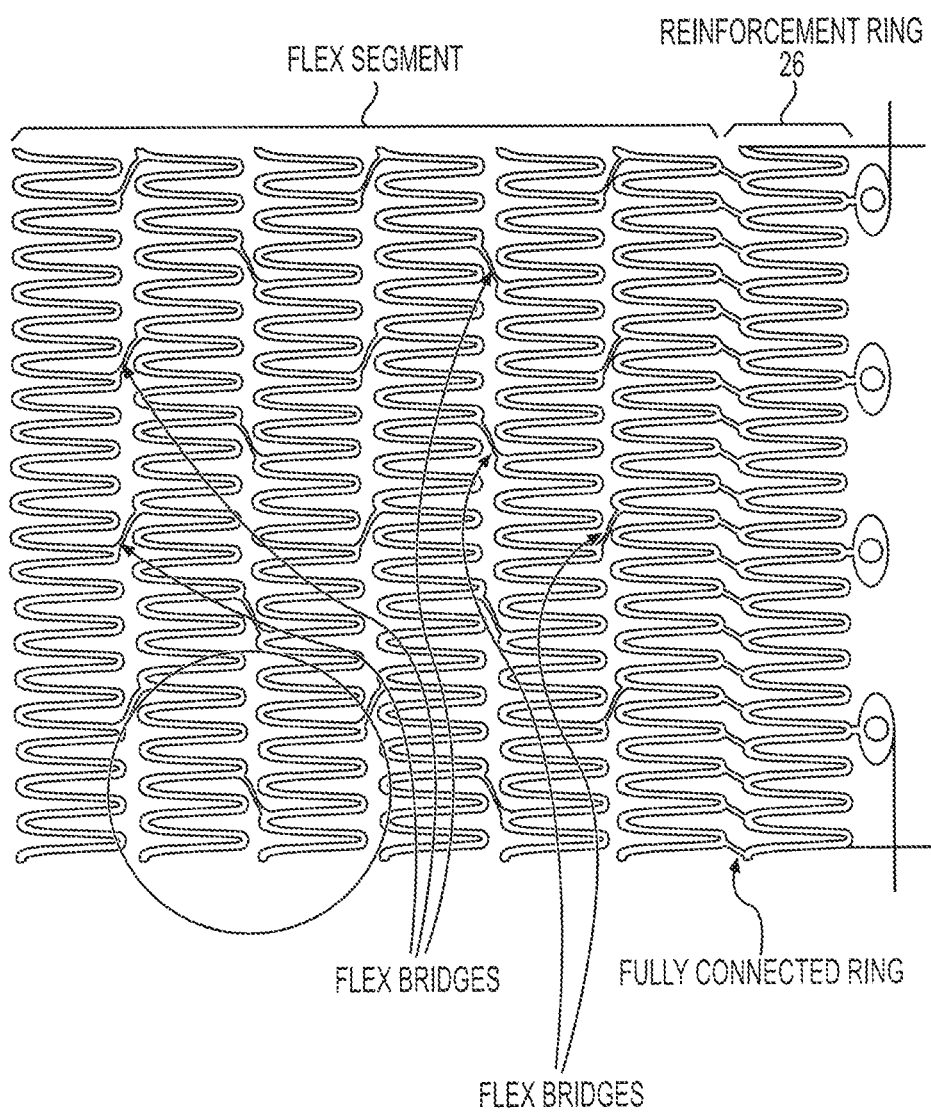
FIG. 7 illustrates an exemplary reinforcement ring according to principles of the present disclosure.

An exemplary embodiment of the reinforcement ring is illustrated in FIG. 7. As can be seen in FIG. 7, more of the ring struts making up the reinforcement ring are connected by flexible connectors/bridges to the adjacent ring than in the neighboring highly flexible segment.

Returning to the stent structure, as illustrated in FIG. 6, a length of stent 10 having length L0 includes high radial force segment 14 having a radial force and/or crush resistance RF1 and a flexibility F1 along the length L1 of the high radial force segment 14. That is, a radial resistive force RF1 of the high radial force segment 14 is relatively greater than the remainder of the stent 10, and may be in the range of 0.75 to 1.00 N/mm, for example. The flexibility F1 of the high radial force segment 14 may also be relatively lower than the remainder of the stent 10. Flexibility is evaluated/measured through angle of deflection. According to principles described herein, the high radial force segment may be designed to withstand long term durability (fatigue) testing with a flexion range of 0-60 degrees.

The relatively high radial force segment 14 is intended to be placed in a vessel in the region of the vessel prone to compression or crushing, such as pinching/crushing of the underlying left common iliac vein 1601 against the vertebra 1602 caused by May-Thurner syndrome, as illustrated in FIG. 3. The high radial force segment has a diameter D1.

The length of stent L0 also includes a highly flexible segment 18, which has relatively greater flexibility than the high radial force 14 segment along the length of the highly flexible segment 18. In addition, according principles of the present disclosure, the highly flexible segment 18 has a length L2, a diameter D2 and radial force, crush resistance RF2 and flexibility F2, where RF2<RF1 and F2>F1, such that the highly flexible segment is more flexible than the high radial force segment 14. According to principles described herein, the highly flexible segment may be designed to withstand long term durability (fatigue) testing with a flexion range of 0-140 degrees. A radial resistive force RF2 of the highly flexible segment 18 may be in the range of 0.50 to 0.70 N/mm, for example.

The length of stent 10 may also include a transition segment 22 between the high radial force segment 14 and the highly flexible segment 18, where the transition segment 22 has a length L3, a diameter D3 and radial force or radial resistive force (crush resistance) RF3 and flexibility F3, where RF1>RF3>RF2 and F1 and F2>F3>F1. The radial force or radial resistive force (crush resistance) RF3 and flexibility F3 of the transition segment 22 may vary over the length L3 of the transition segment 22 or may be constant along the length L3 of the transition segment 22.

Each of the high radial force segment 14, transition segment 22 and highly flexible segment 18 has a different radial force, crush resistance and flexibility, which may be provided by different ring structures in each segment of the stent 10. As can be observed in FIG. 6, a high radial force segment 14 may have a cell structure that has relatively greater periodicity, may be formed of stiffer ring struts and flexible connectors, and/or may have a more closed cell structure or other structure to impart the desired radial force or crush resistance relative to the radial force or crush resistance of the highly flexible segment. For example, the strut geometry, thicker/wider struts provide more radial strength, number of apexes around the circumference of the stent/ring geometry can all drive radial force up or down, and the configuration/connection to the adjacent rings through the bridge connectors and more ring connectors can increase radial force. Similarly, the highly flexible segment 18 may have a cell structure that has relatively lesser periodicity, may be formed of relatively more flexible ring struts and flexible connectors, and/or have a more open cell structure. The transition segment may have a cell structure that transitions a geometry of the rings struts and flexible connectors of the high radial force segment to a geometry of the highly flexible segment, or the transition segment may have a different cell structure than the high radial force segment and the highly flexible segment. In an embodiment according to principles described herein, the stent having a high radial force segment, a transition segment and a highly flexible segment may be cut from a single tube, such as nitinol, for example, but may also be formed by any other suitable means.

In the illustrated embodiment of FIG. 6, each of the segments of the stent has substantially the same diameter, such that $D1 \approx D2 \approx D3$. (As described hereinbelow, such as in the context of FIG. 15, the stent could also have varying diameters that, when combined with the structural and material characteristics described above and below can achieve a flexible segment with a reduced loss in radial stiffness.) As described herein, one stent can treat a range of vein vessel diameters. The present stent structure may allow a single stent to treat multiple vessel sizes as the force exerted on the vessel remains fairly consistent over a range of diameters (3-4 mm). This is different than conventional stents in that most conventionally stents need to be specifically sized to the vessel they are treating (i.e., 0.5 mm-1.0 mm of oversizing). Thus, most conventional stents are offered in 2 mm increments (e.g., 10 mm, 12 mm, 14 mm, etc.). Adaptive diameter according to principles described herein simplifies sizing decisions for the doctor and allows a single stent to treat a long segment of vein, as the vein diameter generally reduces in diameter in the proximal direction.

It is contemplated that the length L2 of the highly flexible segment 18 will be greater than the length L1 of the high radial force segment which will be greater than the length L3 of the transition segment.

Figure 8:
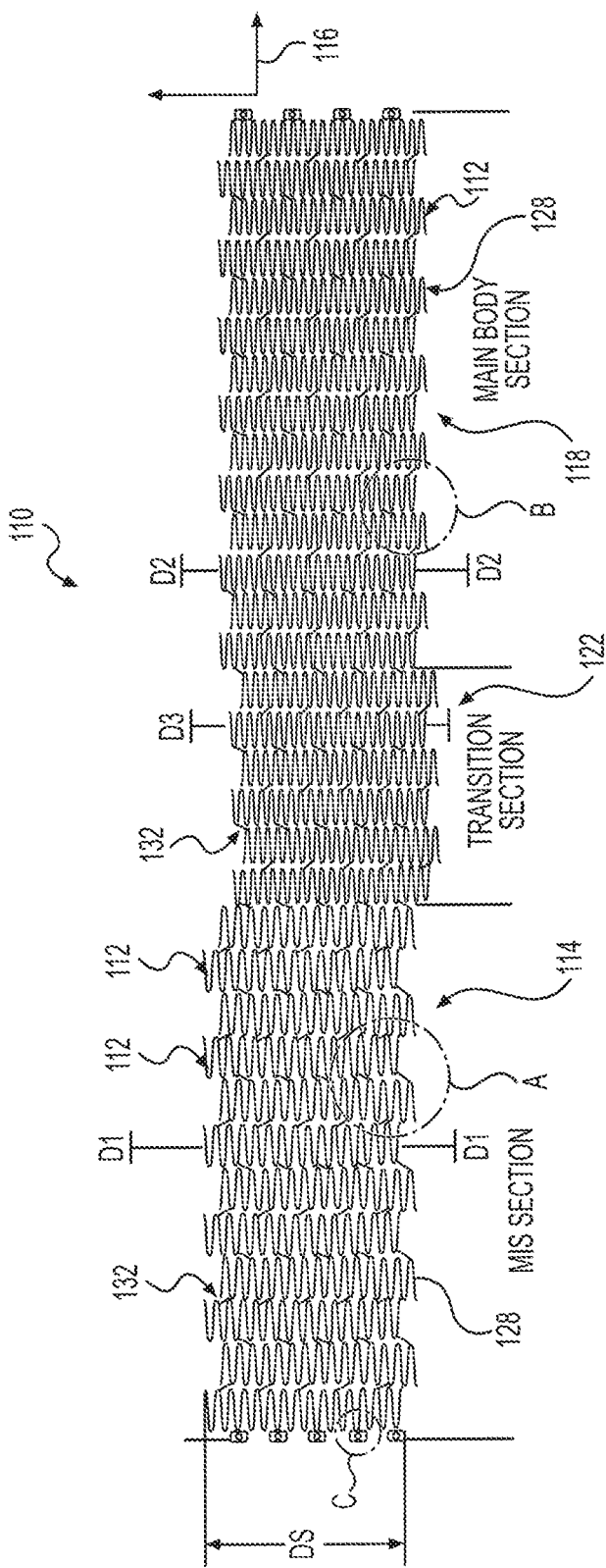
FIG. 8 illustrates an exemplary embodiment of a hybrid stent according to principles of the present disclosure.

An exemplary embodiment structure of a stent 110 according to principles of the present disclosure is shown in FIG. 8. As illustrated in FIG. 8, the diameter DS along the stent 110 at any given ring 112 is substantially the same ($D1 \approx D2 \approx D3$). In the embodiment illustrated in FIG. 8, each of the high radial force segment (May-Thurner Syndrome "MTS" Section) 114, the transition segment (Transition Section) 122 and the highly flexible segment (Main Body Section) 118, has a similar cell pattern. In such case, the radial force or crush resistance RF of the segments may be varied by varying the thickness of the struts and/or flexible connectors 132 or the angular relationship of the struts with other struts and/or with the flexible connectors and/or the angulation of the flexible connectors themselves.

It should be noted that terms such as perpendicular, thickness, same, similar, and other dimensional and geometric terms should not be regarded as strict or perfect in their application. Instead, geometric and other dimensional reference terms should be interpreted based on their correspondence to accepted manufacturing tolerances and functional needs of the stent 110 on which they are employed. For example, the term "perpendicular" should be appreciated as affording a reasonable amount of angular variation due to manufacturing imperfections or the actual intentional curves cut or formed in the stent design 110. Also, any thickness, width or other dimension should be assessed based on tolerances and functional needs of the design rather than idealized measurements.

Figure 15:
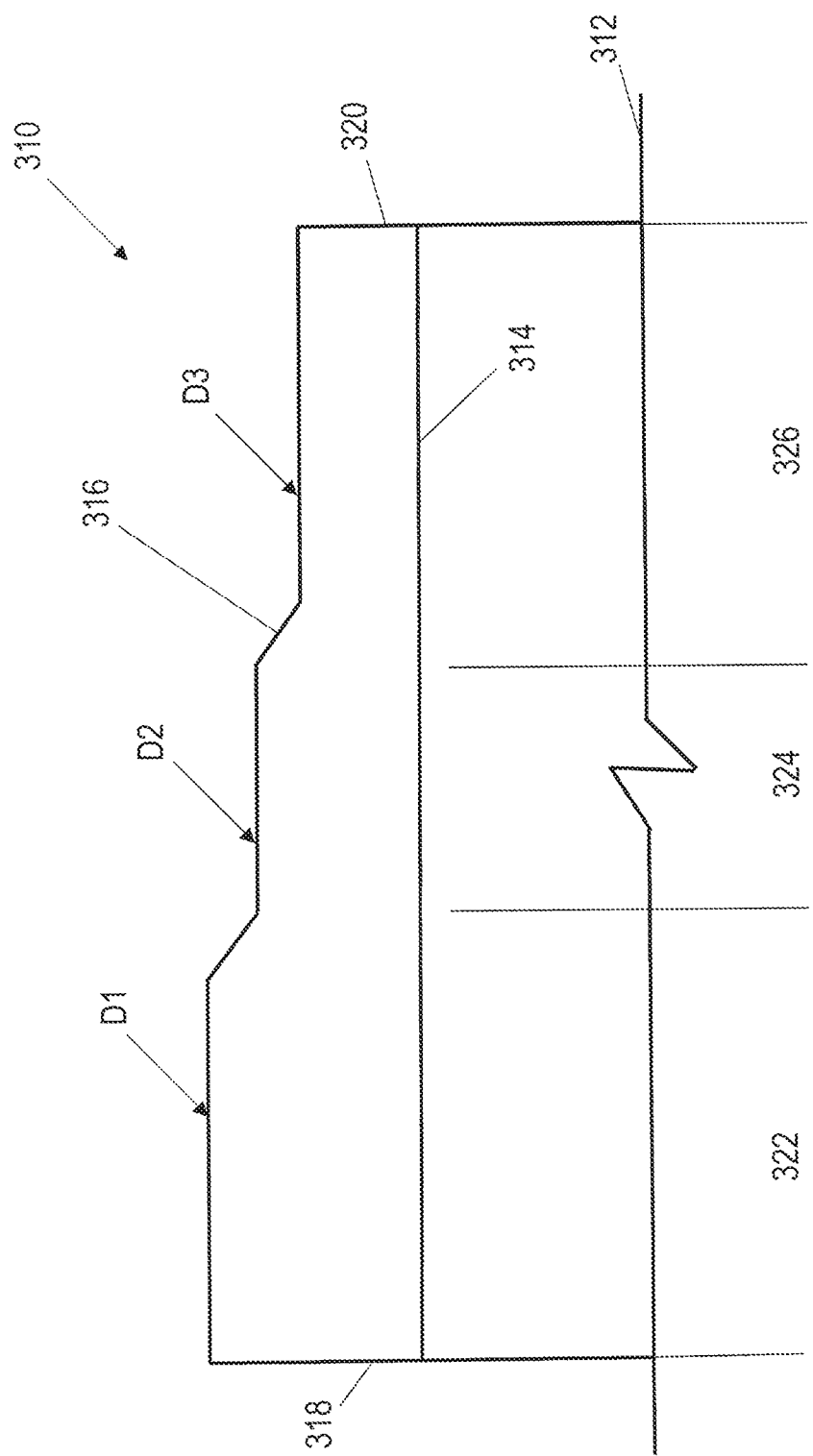
FIG. 15 illustrates an exemplary hybrid stent with a tapering wall thickness.

The thickness of the strut 128, on the other hand, is its depth in the radial direction which is generally perpendicular to the strut width measurement, as shown in FIG. 8. The strut thickness 128 normally corresponds to the wall thickness (outside diameter minus inside diameter) of the tube from which the stent 110 is laser cut after etching, grinding and other processing. Below, associated with FIG. 15, is a description of how varying wall thickness (and hence strut thickness) can alter stent radial stiffness and flexibility. But, embodiments of the stents disclosed herein are not necessarily limited to being laser-cut from a cylindrical tube with a predetermined wall thickness. They could also be formed or cut from flat sheets that are welded together at long edges to form a tube-like structure.

Each of the rings 112 is comprised of a plurality of ring struts 128 interconnected to form alternating peaks or apexes 120 and troughs 124. As shown in FIG. 8, each of the ring struts 128 is generally straight. In one embodiment shown in FIGS. 8-9, a stent 110 includes a plurality of rings 112 connected by a plurality of flexible connectors 132. The rings 112 are arranged in a spaced relationship along a long axis 116 of the stent 110. The connectors 132 extend between adjacent pairs of the rings 112. Each of the rings 112 and connectors 132 are comprised of a plurality of interconnecting struts. The dimensions and orientation of these struts are designed to provide flexibility and radial stiffness according to principles of the present disclosure.

The exemplary hybrid stent 110 illustrated in FIG. 8 may be made of Nitinol tubing that is superelastic per ASTM F2063. The stent specification may further be as follows, post eletropolishing: AF temperature of parts to be 19+/−10 degrees Celsius. The hybrid stent may be designed to treat a range of iliofemoral veins ranging in size from 12 mm to 20 mm. These dimensions are exemplary and a stent according to principles of the present disclosure are not so limited.

Figure 9A:
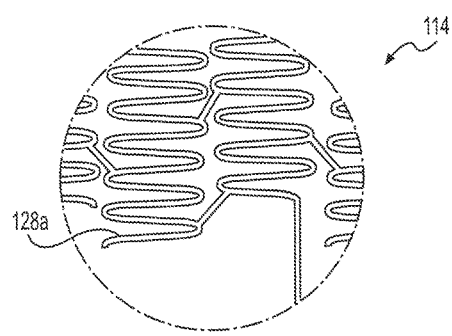
FIG. 9A, FIG. 9B and FIG. 9C illustrate details of the embodiment of FIG. 8.
Figure 9B:
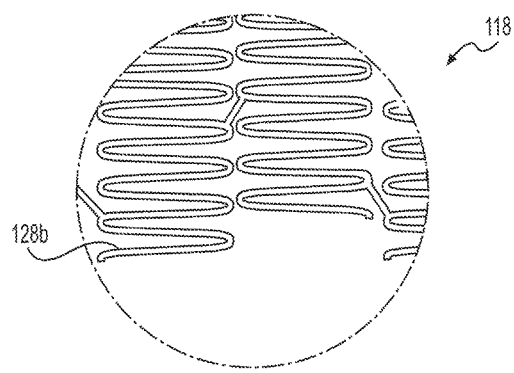
Figure 9C:
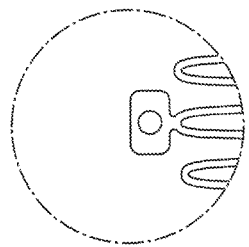

FIGS. 9A, 9B and 9C illustrate details of the strut and connector structure of the high radial force segment 114 (FIG. 9A) and the highly flexible segment 118 (FIG. 9B) of the embodiment FIG. 8 at the locations indicated in FIG. 8. FIG. 9C is showing detailed dimensions of the eyelet 119 geometry in which a radiopaque (RO) marker will be inserted to aid the doctor with deployment location of the stent under fluoroscopy.

FIG. 9A illustrates ring struts 128a of the high radial force segment 114. FIG. 9B illustrates ring struts 128b of the highly flexible segment 118.

As can be appreciated, foreshortening of the stent can be a particular problem for placement of a stent. In practice, stents with greater flexibility tend to foreshorten more. As discussed above, accurate placement is ideal in all medical interventions, but it is of great interest in areas where the end that is first deployed is critical. Such areas include at vessel bifurcations and branch vessels, so that the implant does not enter or interfere with the portion of the vessel that does not require treatment. Such a bifurcation is present at the inferior vena cava where it branches into right and left iliac veins, as described in more detail below.

Figure 10:
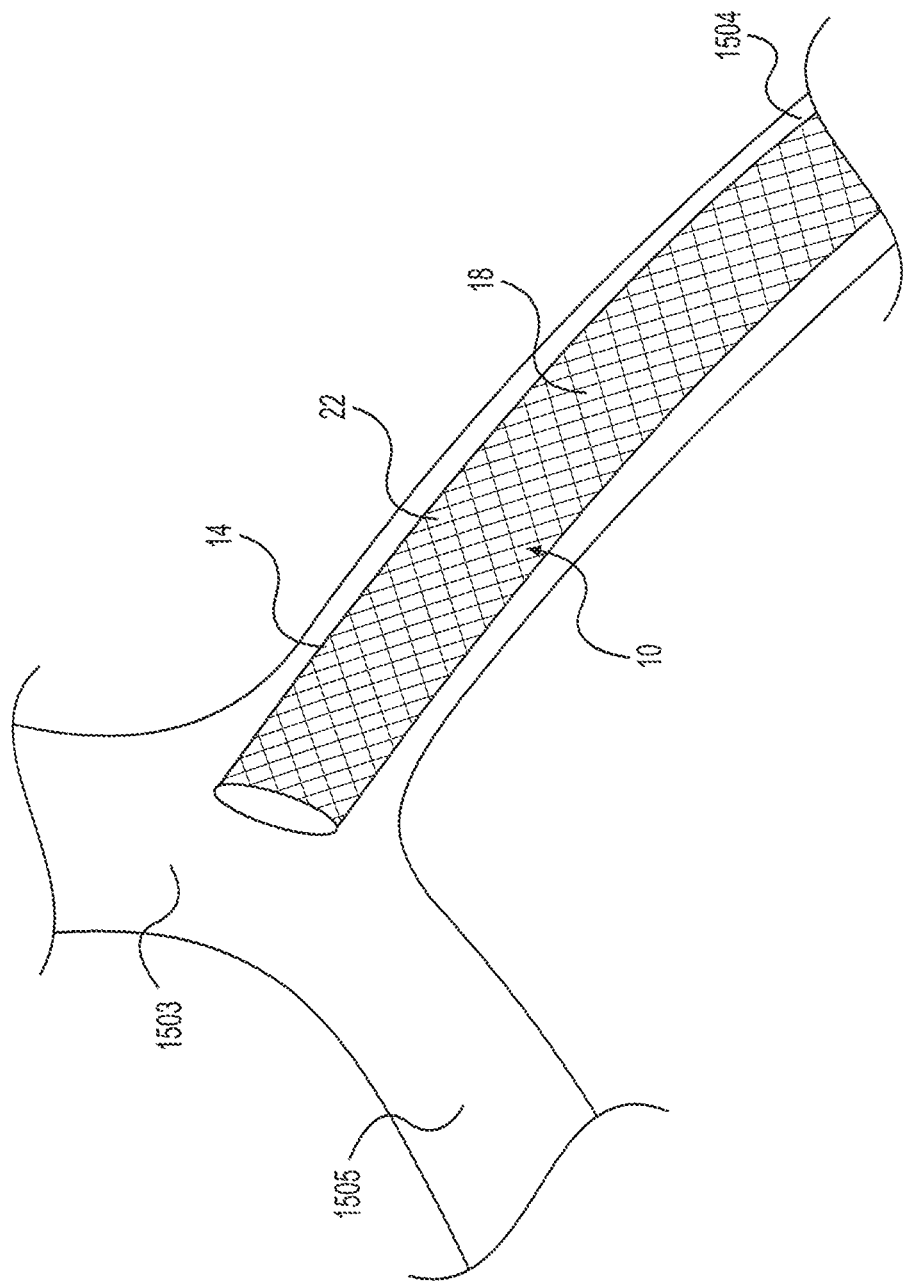
FIG. 10 illustrates an exemplary placement of a hybrid stent according to principles of the present disclosure in the left common iliac vein.

As described herein, a stent according to principles described herein includes a high radial force segment and a highly flexible segment. The high radial force segment, with its stiffer structure, will foreshorten less than the highly flexible segment, and as a result, can allow for more accurate placement in the vessel into which it is implanted. FIG. 10 illustrates a rough placement of a stent according to principles of the present disclosure. FIG. 10 illustrates the inferior vena cava 1503 branching into the left common iliac vein 1504 and right common iliac vein 1505. It will be understood that the rough diagram illustrated in FIG. 10 represents the view looking down on a patient laying face-up (i.e., an anterior-poster view of the patient at the location of the bifurcation of the inferior vena cava 1503). For sake of simplicity, the abdominal aorta and its branching are not shown in FIG. 10, but are shown in FIG. 2, above.

As illustrated in FIG. 10, a multi-segment stent 10 according to principles described is placed in the left common iliac vein 1504. The high radial force segment 14 of the stent 10 may be allowed to extend into the iliac vein 1503, although the end of the high radial force segment is intended to be placed to be at the junction of the left common iliac vein 1504 and the iliac vein 1503. The highly flexible segment 18 extends away from the high radial force segment 14 and the transition segment 22 between the highly flexible segment 18 and the high radial force segment 14.

Figure 11:
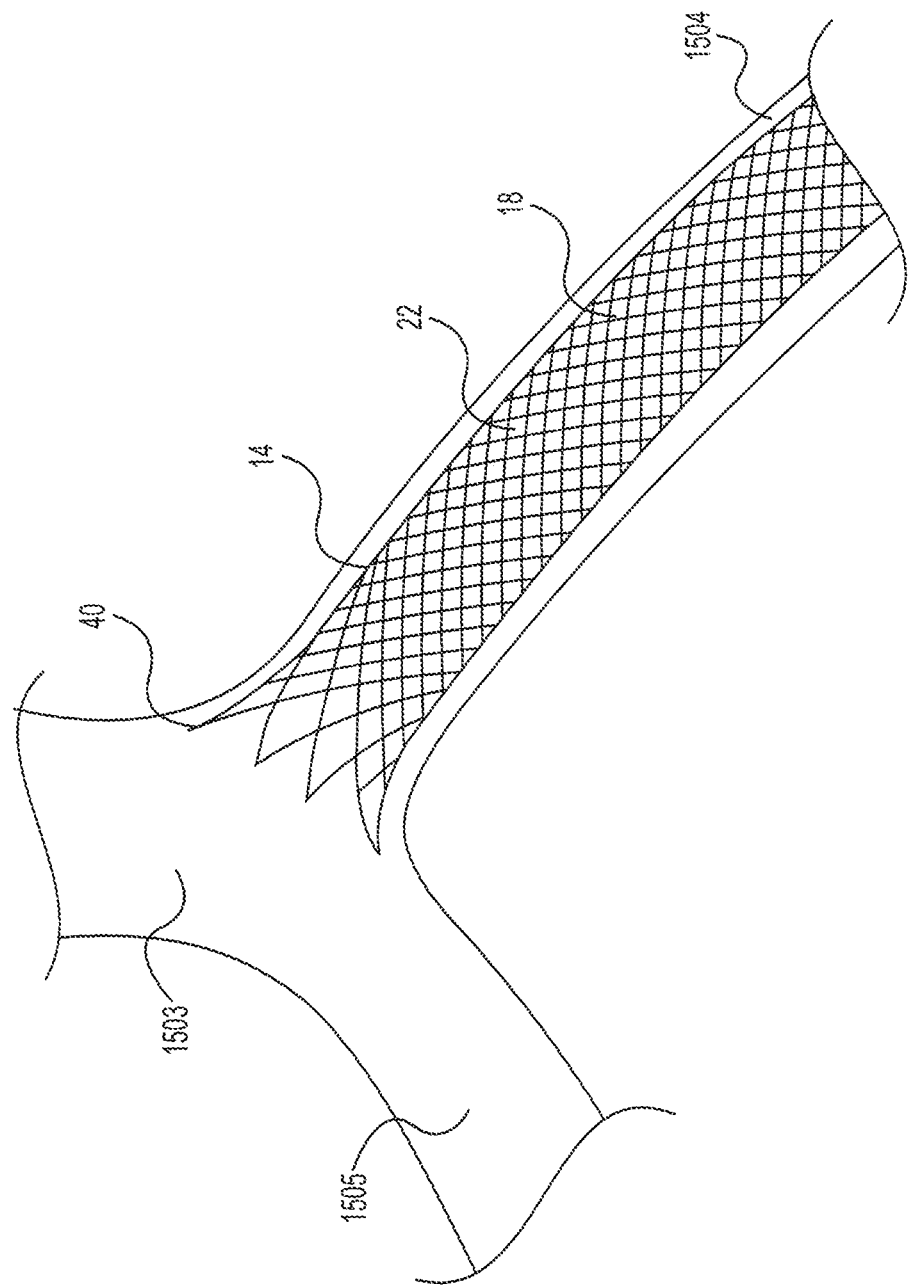
FIG. 11 illustrates an exemplary placement of a hybrid stent having a flared end according to principles of the present disclosure in the left common iliac vein.

To facilitate placement of the stent 10 at the junction of the left common iliac vein 1504 and the iliac vein 1503, the stent 10 may have a flared end adjacent the high radial force segment 14, as illustrated in FIG. 11. The distal flared section is controlled by radius 'r'. Exemplary flare sizes include 2.5 mm×5.0 mm and 5.0 mm×5.0 mm, but stent flares according to principles of the present disclosure are not so limited. The flared distal end of the stent may be used for placement of the stent at a bifurcation of two vessels such as the common iliac vein 1504 and the iliac vein 1503. The pre-loaded stent configuration on the delivery system described herein allows the distal flared section of the stent to be partially deployed from the delivery system allowing the operator to position the flared section of the stent at the bifurcation of two vessels. The delivery catheter is advanced central to the vessel bifurcation to be treated, in this case the left common iliac vein 1504. If radiopaque markers are provided on the implant, the operator can seat the partially deployed flare section of the stent at the bifurcation junction using the radiopaque markers. Once the central flared end of the partially deployed stent is in the appropriate deployment location and seated at the bifurcation junction the remainder of the stent can be deployed.

Figure 12:
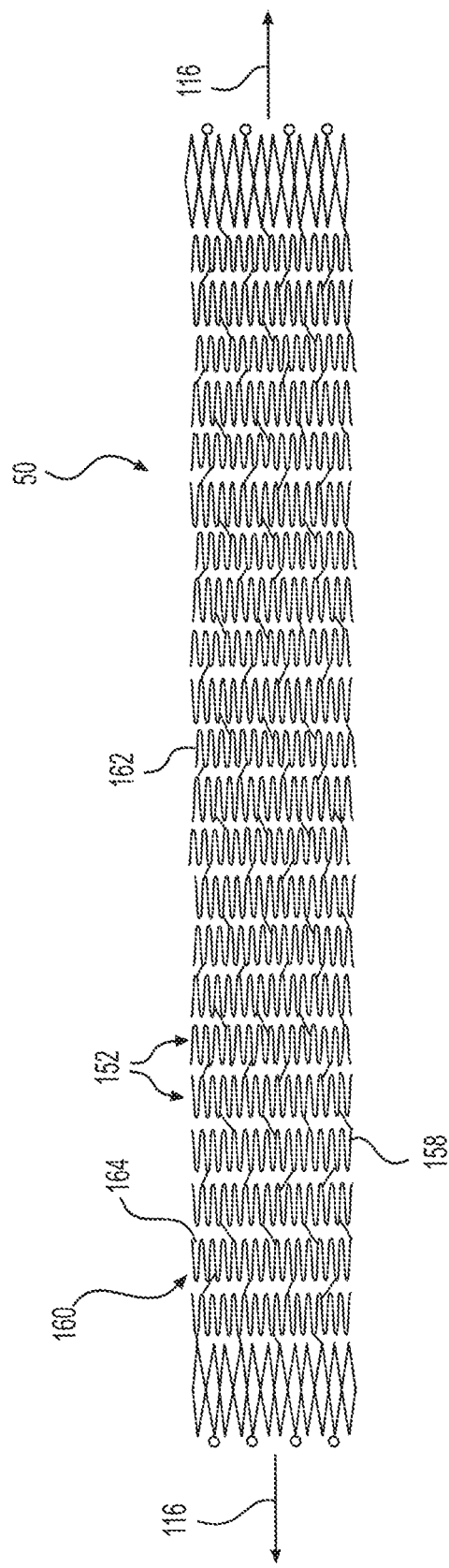
FIG. 12 illustrates an exemplary extension stent according principles of the present disclosure.

In an aspect of the present invention, a separate extension stent 50 may be included along with the stent 10. An embodiment of the separate extension stent 50 is illustrated in FIG. 12. As illustrated in FIG. 12, the separate extension stent 50 is tubular and may be a highly flexible segment similar to the highly flexible segment 18 in the hybrid stent 10 described above. In an aspect of the present disclosure, the separate extension stent 50 may comprise a plurality of rings 152, which comprise a plurality of ring struts 158 interconnected to form alternating peaks or apexes 160 and troughs 164. As shown in FIG. 12, each of the ring struts 158 are generally straight. The ring struts 158 may be connected to flexible connectors 162. The rings 152 are arranged in a spaced relationship along a long axis 116 of the stent 110. The connectors 162 extend between adjacent pairs of the rings. The separate extension stent 50 may also include reinforcement rings on either or both ends of the tube. The dimensions and orientation of these struts are designed to provide flexibility and radial stiffness according to principles of the present disclosure. Each of the rings 152 and connectors 162 comprises a plurality of interconnecting struts. The separate extension stent is made of an expandable material or a self-expandable material, such as Nitinol. The separate expansion stent 50 may be cut from a single tube, such as nitinol, for example, but could also be formed or cut from flat sheets that are welded together at long edges to form a tube-like structure.

Figure 13:
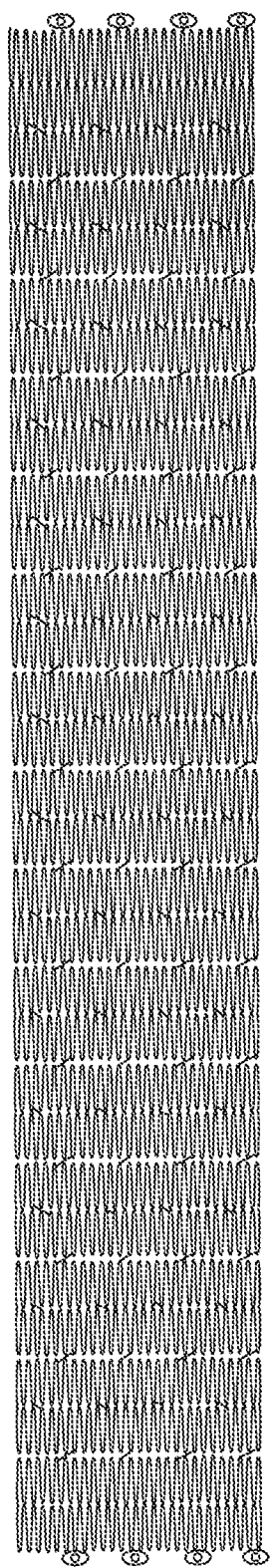
FIG. 13 illustrates an embodiment of an extension stent according to principles of the present disclosure.

An exemplary extension stent is illustrated in FIG. 13. The extension stent illustrated in FIG. 13 may be made of nitinol tubing that is superelastic per ASTM F2063. The stent specification may further be as follows, post electropolishing: AF temperature of parts to be 19+/−10 degrees Celsius. The extension stent may be designed to treat a range of iliofemoral veins ranging in size from 8 mm to 16 mm. These dimensions, as well as dimensions illustrated in the figures, are exemplary and a stent according to principles of the present disclosure are not so limited.

Figure 14:
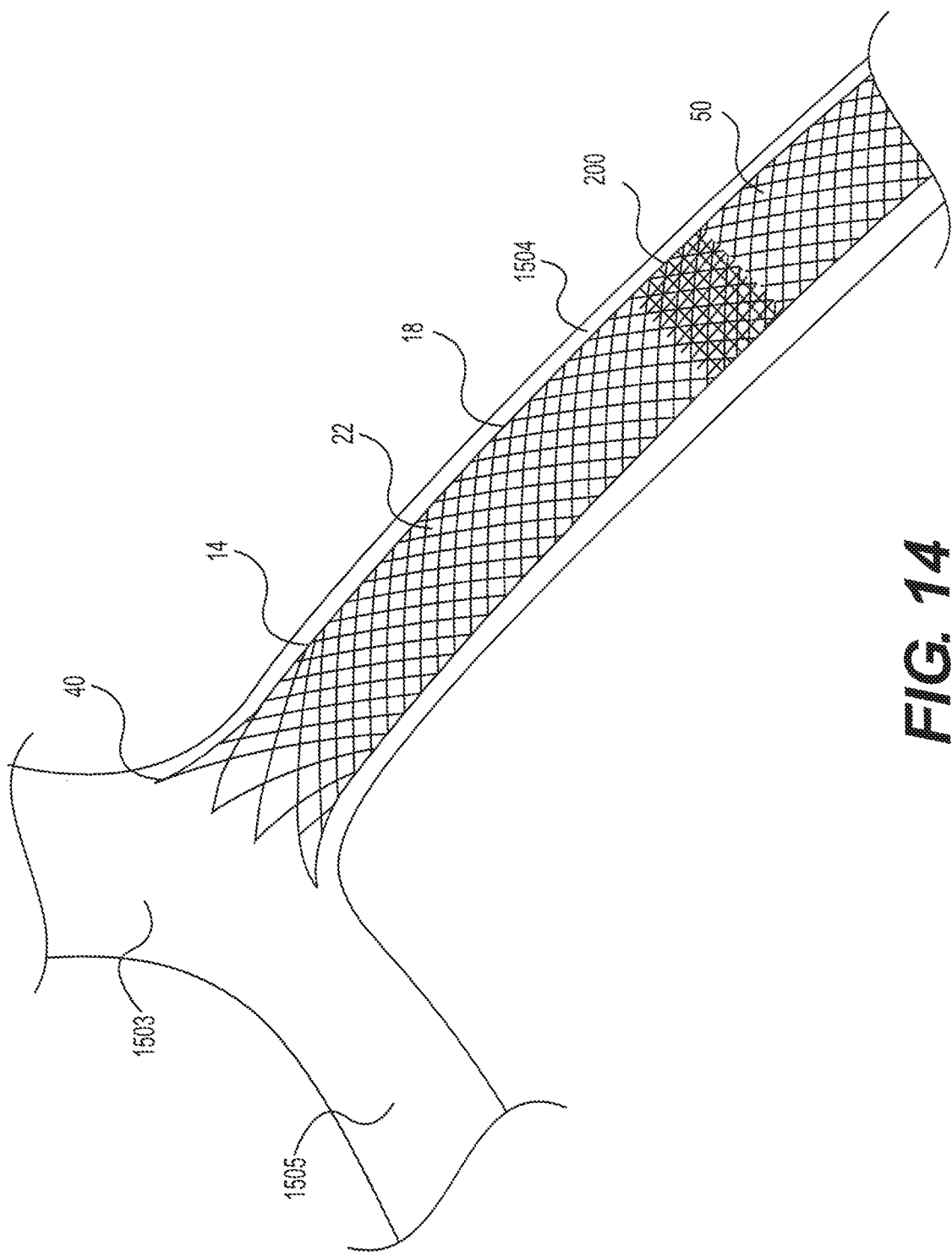
FIG. 14 illustrates an exemplary placement of a hybrid stent and an extension stent according to principles of the present disclosure in the left common iliac vein.

The separate extension stent 50 is placed in the left iliac vein 1504 adjacent the highly flexible segment 18 of the hybrid stent 10 and may overlap the end of hybrid stent 10, as illustrated in FIG. 14. The region of overlap in the illustration is indicted by reference number 200. The placement of the hybrid stent 10 and the separate extension stent 50 may be performed using the same delivery device at the same time. A second delivery catheter with pre-crimped extension stent may be introduced into the treatment vessel and approximate the proximal end of the previously deployed hybrid stent. The catheter with crimped extension stent would be inserted into the proximal end of the hybrid stent, positioned and the stent would be deployed utilizing the radiopaque markers on both stents to achieve appropriate overlap, e.g., 1 cm. In another aspect, the extension stent can be implanted as a stand-alone stent.

It should be noted that an extension stent as described herein may be used in combination with other stents as a "main stent", besides the hybrid stent 10. In use, the extension stent can be used to allow for variation in placement.

In addition, the extension stent may include reinforcement rings where the reinforcement ring may be an area of greater stiffness/crush resistance at an end portion of the stent. "Greater stiffness" here means having a stiffness greater than a portion of the sent adjacent the reinforcement ring. The reinforcement ring having greater stiffness may provide good inflow into the stent and through the vessel having the implant therein. The reinforcement rings may make the extension stent easier to place with respect to the main stent, for example, by mitigating crushing of the ends as they are made to overlap. In addition, to facilitate placement, the ends of the extension stent and/or the stent to which it is to be placed adjacent can be coated with a polymer, such as urethane or PTFE. Also, the extension stent may include anchors, eyelets, radiopaque markers or other features to assist in placement of the extension stent. The extension stent may also be delivered with the main stent, or may be separately delivered to the vessel.

The extension stent may be delivered via an appropriate access site, (e.g. jugular, popliteal, etc.). The extension stent can be made to be "bidirectional", such that it could be preloaded onto a delivery catheter without specific regard to the direction of the delivery (e.g., jugular, popliteal, etc.). E.g., the delivery can be made from above the treatment region or from below the treatment region. Such bidirectionality can be facilitated by the extensions stent geometry being symmetrical such that ends of the extension stent have the same geometry. The stent may be delivered by a coaxial delivery catheter. In another aspect of the present disclosure, a novel delivery device may include a cartridge that may be loaded onto a catheter and the hybrid sent also loaded on the catheter. The cartridge can be flipped by the operator for retrograde or anterograde. The stent may be preloaded onto the delivery catheter for the direction of the delivery (e.g., jugular, popliteal, etc.)

As can be appreciated, the actual stent ring geometry may vary from that disclosed herein, as long as the stent 10 includes a first section with a relatively greater radial force or crush resistance than a second section of the stent that has a relatively greater flexibility than the first section. It is also contemplated that the separate extension stent 50 have a flexibility similar to the highly flexible segment of the hybrid stent 10. Exemplary stent geometries for segments of the hybrid stent 10 and the extension stent 50 are taught in U.S. patent application Ser. Nos. 15/471,980 and 15/684,626, which are hereby incorporated by reference for all purposes as if fully set forth herein.

For example, it is noted that the struts of the rings and flexible connectors with structure, including areas of expanded or reduced width or thickness, to account for venous applications may be used. For example, an improved combination of high radial resistive force and increased flexibility extending distally down the stent can be achieved by tapering the wall thickness of the nitinol tube used to fabricate the stent. The tube wall thickness could be tapered slightly, constantly or in steps, along its length. Tapering wall thickness could be combined with changes to the strut pattern to make the wall structure slightly more robust as you move distally. This reduces the typical decrease in radial resistive force associated with the thinning wall. This can create the "goldilocks" scenario of improving distal flexibility without giving up much radial resistive force.

FIG. 15, for example, shows another embodiment of a hybrid stent 310 wherein the various segments or regions have varying radial stiffness and flexibility along an axis 312 of the stent. In particular, FIG. 15 is a schematic of the wall thickness (and when struts are employed, strut thickness) of the tubular stent 310 having a constant inside diameter formed by inside surface 314, an outside surface 316 with varying diameter and first and second free ends 318, 320, respectively. Between these features is the material of the stent body that may also include various structures, such as rings and connectors formed by struts as described elsewhere herein (although not shown in FIG. 15). Thus, the tapering wall structure can be combined with modifications to the materials and strut pattern in the distal direction to have the "goldilocks" scenario of maintaining good resistive forces while still improving flexibility.

Returning to FIG. 15, the hybrid stent 310 includes a firm region 322, a transition region 324 and a flexible region 326 that correspond to a first diameter (D1), a second diameter (D2) and a third diameter (D3), respectively. Due to the grinding, cutting, drawing or other operation the first diameter is greater than the second diameter which is greater than the third diameter. In between the diameters are frustoconical regions formed by the transition between diameters for smoother, less-invasive surface. In other embodiments, the reduction in wall thickness may be smooth and continuous—without an abrupt transition between the different regions. In such a case, regions may overlap with each other and/or have indistinct boundaries such that their function may depend on the application. The inside diameter remains, in the illustrated embodiment, relatively constant—for example when the stent is formed from stock tube and the inside is not selectively machined. The regions could also be formed by a combination of reduced inner diameter and outer diameter, or just reductions in the inner diameter. Additionally, the first and second free ends 318, 320 may be reinforced and/or flared for anchoring and maintaining patency to encourage blood flow as described above.

At least partially as a result of the diameter variations, the firm region has a greater stiffness (radial resistive and/or crush force) than the transition region which has a greater stiffness than the flexible region. Generally, for treating the May-Thurner Syndrome, the radial stiffness of the firm region should be sufficient to maintain sufficient venous patency to reduce or eliminate the MTS symptoms. Meanwhile, the transition and flexible regions 324, 326 should have sufficient flexibility (for applications treating MTS) to withstand the high repetition, high bending loads described elsewhere herein. But, the loss of wall thickness in the more flexible regions 324, 326 is mediated somewhat by the structures described throughout the instant application, such as increased strut density, more closed cells, increased connectors between rings, to still allow those regions to help maintain patency and venous blood flow.

The hybrid stent 310 can be formed, for example, by starting with a stock tube of constant inside and outside diameter and then using centerless grinding to form the regions. Other approaches can include step drawing the tube through dies with intervening annealing phases. Also, the tube can be preconditioned after modification or during intervening steps to prepare it for use.

In another embodiment, the radial stiffness and flexibility of the hybrid stent 310 can be tailored using centerless grinding. Centerless grinding includes use of a stationary wheel and a moving wheel with the workpiece (the nitinol tube) placed between the two wheels. The nitinol tube can also be supported on a work rest to keep it in position between the two opposing wheels. The two wheels rotate at different speeds. The stationary wheel (or grinding wheel) is on a fixed axis and rotates such that the force applied to the nitinol tube is directed downward against the work rest. The other wheel (or regulating wheel), translates in the direction of the stationary wheel and thus applies lateral pressure to the nitinol tube. The stationary wheel performs a grinding action by having a higher tangential speed than the nitinol tube at the point of contact. The grinding wheel, by turning faster, removes chips of material at the point of contact. The speed of the two wheels relative to each other provides the grinding action and determines the rate a which material is removed from the nitinol tube.

Centerless grinding may be applied to the inside of the tube also, by, for example, having the stationary or moving wheel inside the tube and the other wheel outside the tube. When the stationary wheel is inside the nitinol tube, the inside of the nitinol tube is ground down to selectively decrease the wall thickness. In any case, centerless grinding can be used at preselected axial lengths of the nitinol tube to create step changes in thickness, such as those shown and described in FIG. 15, a tapered wall (which can be achieved through an end-feed—feeding the nitinol tube axially through the centerless grinding machine—for example) or even more complex shapes, like an hourglass. Generally, in-feed centerless grinding works well for creating a hybrid stent 310 because the moving wheel can be moved in and out of contact with the nitinol tube within axial lengths of the tube larger than the width of the moving wheel.

Varying wall thickness, including varying wall thicknesses generated by centerless grinding, can be applied also to the extension stent 50 described hereinabove. Centerless grinding, for example, can be used to reduce the thickness of the reinforcement rings at the end of the extension stent 50 to improve the flexibility of the ends while retaining most of the stiffness imbued in the reinforcement rings. Referring to FIG. 12, the reinforcement rings at the ends of the stent 50 include a closed cell structure that is stiffer than the remaining structure between the ends. Reducing the wall thickness in these ends can improve flexibility without a concomitant loss in radial stiffness of the reinforcement rings. Reducing the outside wall diameter may also allow the extension stent ends to slip more easily within the hybrid stent 310, such as is shown in FIG. 14. Or, conversely, the inside diameter of the extension stent 50 can be reduced to better receive the hybrid stent 310's end.

In any case, it should be noted that the tapering wall thickness can be applied to a range of stent types and locations thereon. Generally, anywhere that a stent may benefit from improved flexibility without a proportionate loss in radial stiffness is a candidate for wall thickness variations.

It should be noted that venous applications benefit from configurations that improve flexibility (due to the greater elasticity of venous applications) while maintaining enough stiffness to resist pressure on the venous structure in selected areas (such as for the May-Thurner syndrome).

Notably, though, the stents herein are not necessarily limited to venous applications unless specifically required by the claims. The disclosed stents could be employed in arterial and biliary applications, for example. But, are particularly suited for the demands of relatively soft structures defining lumens that are subject to much greater bending, twisting, stretching and other contortions and loads than are general arterial lumens.

To deploy the implant, the implant may be radially compressed/crimped to a smaller diameter for loading onto/into a delivery catheter. The implant may be crimped over a balloon on the inner core of the delivery system which may be later inflated to expand the crimped implant to the desired diameter.

Implants such as those described above may advantageously provide an adaptive diameter and/or flexibility to conform the dynamic movement of peripheral veins in leg/pelvis thereby facilitating treatment of both iliac vein compression syndrome and iliofemoral venous outflow obstructions.

It may be desirable to have a stent that will conform to the existing path of a vein instead of a straightening out of the vessel by the stent. It may also be desirable to have a high radial stiffness of the stent to resist collapse of the stent under crushing load and to maximize the resultant diameter of the treated vessel at the location of the stent deployment. With most stent constructions there is a direct relationship between radial stiffness and axial stiffness.

Common commercially available balloon expandable stents experience a dramatic change in length as a balloon is used to expand the stent within the vessel. Common commercially available self-expanding stents experience a change in length less dramatic, but still substantial, which increases with increasing stent length. Change in length between the configuration within the delivery system and when deployed in the vessel causes difficulty in placing/landing the stent precisely at the target location. When the stent is delivered in its crimped configuration, then deployed or expanded, the shortening in length causes the stent target deployment location to have to offset from the target dwell location. The magnitude of this effect is not controllable or easily anticipated as it is dependent on the luminal cross-section along the length of the target dwell location (which is frequently and unexpectedly influenced by residual stenosis, irregular shape due to external objects, and/or forces, etc.). For target lesions leading up to the junction of the left and right iliac into the IVC, this causes difficulty in placing the stent to dwell completely within the iliac along its total length up to the junction to the inferior vena cava without crossing into the inferior vena cava. Placement of a high radial force segment at the junction not only assists in addressing crush by May-Thurner Syndrome, but also may assist in reducing foreshortening from the target location.

Embodiments disclosed herein can be used for both balloon expandable and self-expanding stent designs. The stent designs can be used for all stent interventions, including coronary, peripheral, carotid, neuro, biliary and, especially, venous applications. Additionally, this could be beneficial for stent grafts, percutaneous valves, etc.

Currently available implants are typically loaded and retained onto a delivery system in a crimped configuration and then navigated and deployed in the desired anatomical location where they expand to the implanted configuration. The final implanted configuration can be achieved through mechanical expansion/actuation (e.g., balloon-expandable) or self-expansion (e.g., Nitinol). Self-expanding implants are manufactured from super elastic or shape memory alloy materials. Accurate and precise deployment of a self-expanding implant can be challenging due to a number of inherent design attributes associated with self-expanding implants. The implant may jump/advance from the distal end of the delivery system during deployment due to the stored elastic energy of the material. Additionally, the implant may foreshorten during deployment due to the change in the implant diameter from the crimped configuration to the expanded configuration. Finally, physiological and anatomical configurations, such a placement at or near bifurcations of body lumens, can affect accurate placement of implants. Once the implant is placed within the body lumen there is potential for uneven expansion or lack of circumferential implant apposition to the body lumen which can result in movement, migration or in certain severe cases implant embolization.

In some embodiments, a self-expanding implant designed with sufficient radial force or crush resistance to resist constant compression of the body lumen while providing optimal fatigue resistance, accurate placement, and in-vivo anchoring to prevent movement/migration is provided. Additionally, various methods for deployment and implantation for treating iliac vein compression syndrome and venous insufficiency disease are provided.

In some embodiments, the implant comprises a purposely designed venous implant intended to focally treat iliac vein compression (May-Thurner Syndrome). The implant may be relatively short in length (~60 mm) and may be manufactured from self-expending Nitinol with integrated anchor features to aid in accurate placement and to mitigate migration following implantation. The implant and delivery system are designed for precise deployment and placement at the bifurcation of the inferior vena cava into the right and left common iliac veins.

As another feature, the stents disclosed herein can include anchor members, radiopaque markers, or eyelets, for example, set forth in pending U.S. patent application Ser. Nos. 15/471,980 and 15/684,626, which are hereby incorporated by reference for all purposes as if fully set forth herein.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In addition, while a number of variations of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. Accordingly, it should be understood that various features and aspects of the disclosed embodiments can be combined with or substituted for one another in order to form varying modes of the disclosed invention. Thus, it is intended that the scope of the present invention herein disclosed should not be limited by the particular disclosed embodiments described above, but should be determined only by a fair reading of the claims that follow.

Similarly, this method of disclosure, is not to be interpreted as reflecting an intention that any claim require more features than are expressly recited in that claim. Rather, as the following claims reflect, inventive aspects lie in a combination of fewer than all features of any single foregoing disclosed embodiment. Thus, the claims following the Detailed Description are hereby expressly incorporated into this Detailed Description, with each claim standing on its own as a separate embodiment.

While various embodiments of the present invention have been described above, it should be understood that they have been presented by way of example only, and not limitation. It will be apparent to persons skilled in the relevant art that various changes in form and detail can be made therein without departing from the spirit and scope of the present invention. Thus, the breadth and scope of the present invention should not be limited by any of the above-described exemplary embodiments, but should be defined only in accordance with the following claims and their equivalents.

What is claimed is:

1. A device comprising:
an elongate tubular wall structure defining a lumen extending therethrough and having a first free end and a second free end opposite the first free end, the elongate tubular wall structure having a firm region adjacent the first free end and extending in an axial direction, a transition region extending in the axial, and a flexible region adjacent the second free end and extending in the axial direction, wherein the transition region extends between the firm and flexible regions;
wherein the firm region has a cylindrical profile about the lumen, the transition region has a cylindrical profile about the lumen and the flexible region has a cylindrical profile about the lumen;
wherein the firm region has a constant first wall thickness, the transition region has a constant second wall thickness and the flexible region has a constant third wall thickness;
wherein the constant first wall thickness is greater than the constant third wall thickness and contributes to a crush resistance of the firm region being greater than a crush resistance of the flexible region.

2. The device of claim 1, wherein the constant second wall thickness is less than the constant first wall thickness but greater than the constant third wall thickness and contributes to crush resistance of the transition region being less than crush resistance of the firm region but greater than crush resistance of the flexible region.

3. The device of claim 2, wherein the elongate tubular wall structure includes an inside diameter defining the lumen and wherein the constant first wall thickness is between a first outer diameter and the inside diameter, the constant second wall thickness is between a second outer diameter and the inside diameter and wherein the constant third wall thickness is between a third outer diameter and the inside diameter.

4. The device of claim 2, wherein a radial stiffness of the firm region is sufficient to reduce a degree of compression of a left common iliac vein suffering May-Thurner Syndrome.

5. The device of claim 1, wherein the flexible region has a flexibility that is greater than a flexibility of the firm region.

6. The device of claim 5, wherein the transition region has a flexibility that is greater than the flexibility of the firm region and less than the flexibility of the flexible region.

7. The device of claim 6, wherein a difference between the flexibility of the flexible region and the firm region is greater than a difference between a radial stiffness of the firm region and a radial stiffness of the flexible region.

8. The device of claim 7, wherein flexibility of the elongate tubular wall structure increases faster than radial stiffness drops progressing from the firm region toward the flexible region.

9. The device of claim 7, wherein the elongate tubular wall structure is defined by a plurality of interconnected struts.

10. The device of claim 9, wherein the interconnected struts have a greater density in the flexible region than the firm region.

11. The device of claim 9, wherein the interconnected struts have a greater frequency of interconnection in the flexible region than the firm region.

12. The device of claim 1, wherein the first and second free ends have a radial stiffness greater than the firm, transition and flexible regions.

13. The device of claim 1, wherein the firm region is separated from the transition region by an elongate tubular wall segment having the lumen extending in the axial direction therethrough, the elongate tubular was segment further having a non-constant wall thickness, such that the elongate tubular wall segment has a frustoconical profile.

14. The device of claim 13, wherein the transition region is separated from the flexible region by another elongate tubular wall segment having a cylindrical lumen extending in an axial direction, the another elongate tubular wall segment further having a non-constant wall thickness, such that the another elongate tubular wall segment has a frustoconical profile.

15. The device of claim 14, wherein the lumen defined by the elongate tubular wall structure has a constant width from the first free end to the second free end.

16. The device of claim 14, wherein the frustoconical profile of the elongate tubular wall segment and the frustoconical profile of the another elongate tubular wall segment are oriented in the same direction.

17. The device of claim 14, wherein a base of the frustoconical profile of the elongate tubular wall segment adjacent the firm region is larger than a top of the frustoconical profile of the elongate tubular wall segment and a base of the frustoconical profile of the another elongate tubular wall segment adjacent the transition region is larger than a top of the frustoconical profile of the another elongate tubular wall segment adjacent the flexible region.

18. The device of claim 17, wherein a diameter of the top of the frustoconical profile of the elongate tubular wall segment are substantially the same as a diameter of the base of the frustoconical profile of the another elongate tubular wall segment.

19. The device of claim 1, wherein the transition region is separated from the flexible region by an elongate tubular wall segment having the lumen extending in the axial direction therethrough, the elongate tubular wall segment further having a non-constant wall thickness, such that the elongate tubular wall segment has a frustoconical profile.

* * * * *